(12) United States Patent
Wilson et al.

(10) Patent No.: US 8,591,460 B2
(45) Date of Patent: Nov. 26, 2013

(54) STEERABLE CATHETER AND DILATOR AND SYSTEM AND METHOD FOR IMPLANTING A HEART IMPLANT

(75) Inventors: Jonathan E. Wilson, Amesbury, MA (US); Robert J. St. John, Mansfield, MA (US); Eric W. Conley, South Berwick, ME (US)

(73) Assignee: Cardiosolutions, Inc., Stoughton, MA (US)

( * ) Notice: Subject to any disclaimer, the term of this patent is extended or adjusted under 35 U.S.C. 154(b) by 924 days.

(21) Appl. No.: 12/510,929

(22) Filed: Jul. 28, 2009

(65) Prior Publication Data

US 2010/0022948 A1 Jan. 28, 2010

Related U.S. Application Data

(63) Continuation-in-part of application No. 12/209,686, filed on Sep. 12, 2008.

(60) Provisional application No. 61/061,343, filed on Jun. 13, 2008.

(51) Int. Cl.
*A61M 25/092* (2006.01)
(52) U.S. Cl.
USPC ..................................... 604/95.04
(58) Field of Classification Search
USPC ...................... 604/95.04, 523, 528
See application file for complete search history.

(56) References Cited

U.S. PATENT DOCUMENTS

| | | |
|---|---|---|
| 2,549,731 A | 4/1951 | Wattley |
| 2,625,967 A | 1/1953 | Stull |
| 3,197,788 A | 8/1965 | Segger |
| 3,445,916 A | 5/1969 | Schulte |
| 3,551,913 A | 1/1971 | Shiley et al. |
| 3,586,029 A | 6/1971 | Evers |
| 3,589,392 A | 6/1971 | Meyer |

(Continued)

FOREIGN PATENT DOCUMENTS

| | | |
|---|---|---|
| EP | 0125393 | 11/1984 |
| EP | 1323438 | 2/2003 |

(Continued)

OTHER PUBLICATIONS

Notice of Allowance dated Oct. 31, 2011 issued in U.S. Appl. No. 11/258,828, 10 pages.

(Continued)

*Primary Examiner* — Aarti B Berdichevsky
(74) *Attorney, Agent, or Firm* — Grossman Tucker Perreault & Pfleger PLLC

(57) ABSTRACT

A catheter according to one embodiment may be configured to extend through a transseptal puncture site, a left atrium, and into a left ventricle. The catheter may comprise a shaft defining at least one lumen configured to receive at least one of an implant and/or a dilator, a first steerable actuator coupled to the shaft at a position on the shaft substantially corresponding to the annulus of the mitral valve when the distal end of the shaft is disposed within the left ventricle, and a handle assembly coupled to a proximal end of the shaft. The handle assembly may comprise a first actuator coupled to the first steerable actuator. The first actuator may be configured to apply a force to the first steerable actuator to deflect the shaft about a region proximate to the first steerable actuator.

22 Claims, 25 Drawing Sheets

(56) References Cited

U.S. PATENT DOCUMENTS

| | | |
|---|---|---|
| 3,671,979 A | 6/1972 | Moulopoulos |
| 3,689,942 A | 9/1972 | Rapp |
| 3,714,671 A | 2/1973 | Edwards et al. |
| 3,739,402 A | 6/1973 | Cooley et al. |
| 3,983,581 A | 10/1976 | Angell et al. |
| 4,079,468 A | 3/1978 | Liotta et al. |
| 4,084,268 A | 4/1978 | Ionescu et al. |
| 4,259,753 A | 4/1981 | Liotta et al. |
| 4,291,420 A | 9/1981 | Reul |
| 4,297,749 A | 11/1981 | Davis et al. |
| 4,439,185 A | 3/1984 | Lundquist |
| 4,535,757 A | 8/1985 | Webster, Jr. |
| 4,597,767 A | 7/1986 | Lenkei |
| 4,865,030 A | 9/1989 | Polyak |
| 4,960,424 A | 10/1990 | Grooters |
| 5,002,067 A | 3/1991 | Berthelsen et al. |
| 5,217,484 A | 6/1993 | Marks |
| 5,222,973 A | 6/1993 | Sharpe et al. |
| 5,261,916 A | 11/1993 | Engelson |
| 5,304,195 A | 4/1994 | Twyford, Jr. et al. |
| 5,308,357 A | 5/1994 | Lichtman |
| 5,318,589 A | 6/1994 | Lichtman |
| 5,350,397 A | 9/1994 | Palermo et al. |
| 5,397,351 A | 3/1995 | Pavcnik et al. |
| 5,411,552 A | 5/1995 | Andersen et al. |
| 5,415,667 A | 5/1995 | Frater |
| 5,462,527 A * | 10/1995 | Stevens-Wright et al. ... 604/528 |
| 5,509,428 A | 4/1996 | Dunlop |
| 5,582,607 A | 12/1996 | Lackman |
| 5,611,800 A | 3/1997 | Davis et al. |
| 5,634,936 A | 6/1997 | Linden et al. |
| 5,638,827 A | 6/1997 | Palmer et al. |
| 5,649,949 A | 7/1997 | Wallace et al. |
| 5,653,712 A | 8/1997 | Stern |
| 5,665,100 A | 9/1997 | Yoon |
| 5,776,075 A | 7/1998 | Palmer |
| 5,792,179 A | 8/1998 | Sideris |
| 5,797,958 A | 8/1998 | Yoon |
| 5,814,098 A | 9/1998 | Hinnenkamp et al. |
| 5,840,081 A | 11/1998 | Andersen et al. |
| 5,891,130 A | 4/1999 | Palermo et al. |
| 5,895,391 A | 4/1999 | Farnholtz |
| 5,928,224 A | 7/1999 | Laufer |
| 5,957,865 A | 9/1999 | Backman et al. |
| 5,957,949 A | 9/1999 | Leonhardt et al. |
| 5,989,242 A | 11/1999 | Saadat et al. |
| 5,993,474 A | 11/1999 | Ouchi |
| 6,090,096 A | 7/2000 | St. Goar et al. |
| 6,152,144 A | 11/2000 | Lesh et al. |
| 6,168,614 B1 | 1/2001 | Andersen et al. |
| 6,190,373 B1 | 2/2001 | Palermo et al. |
| 6,217,610 B1 | 4/2001 | Carpentier et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,332,893 B1 | 12/2001 | Mortier et al. |
| 6,358,277 B1 | 3/2002 | Duran |
| 6,415,693 B1 | 7/2002 | Simon et al. |
| 6,419,695 B1 | 7/2002 | Gabbay |
| 6,440,132 B1 | 8/2002 | Jackson |
| 6,454,798 B1 | 9/2002 | Moe |
| 6,461,382 B1 | 10/2002 | Cao |
| 6,482,228 B1 | 11/2002 | Norred |
| 6,508,825 B1 | 1/2003 | Selmon et al. |
| 6,592,606 B2 | 7/2003 | Huter et al. |
| 6,652,578 B2 | 11/2003 | Bailey et al. |
| 6,673,100 B2 | 1/2004 | Diaz et al. |
| 6,682,559 B2 | 1/2004 | Myers et al. |
| 6,695,866 B1 | 2/2004 | Kuehn et al. |
| 6,746,404 B2 | 6/2004 | Schwartz |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,821,297 B2 | 11/2004 | Snyders |
| 6,830,584 B1 | 12/2004 | Seguin |
| 6,830,585 B1 | 12/2004 | Artof et al. |
| 6,849,081 B2 | 2/2005 | Sepetka et al. |
| 6,869,444 B2 | 3/2005 | Gabbay |
| 6,896,700 B2 | 5/2005 | Lu et al. |
| 6,911,043 B2 | 6/2005 | Myers et al. |
| 6,971,998 B2 | 12/2005 | Rosenman et al. |
| 6,974,476 B2 | 12/2005 | McGuckin, Jr. et al. |
| 7,018,406 B2 | 3/2006 | Seguin et al. |
| 7,056,286 B2 | 6/2006 | Ravenscroft et al. |
| 7,070,618 B2 | 7/2006 | Streeter |
| 7,077,862 B2 | 7/2006 | Vidlund et al. |
| 7,101,395 B2 | 9/2006 | Tremulis et al. |
| 7,112,219 B2 | 9/2006 | Vidlund et al. |
| 7,160,322 B2 | 1/2007 | Gabbay |
| 7,189,199 B2 | 3/2007 | McCarthy et al. |
| 7,247,134 B2 | 7/2007 | Vidlund et al. |
| 7,344,553 B2 | 3/2008 | Opolski et al. |
| 7,374,572 B2 | 5/2008 | Gabbay |
| 7,381,210 B2 | 6/2008 | Zarbatany et al. |
| 7,404,824 B1 | 7/2008 | Webler et al. |
| 7,657,326 B2 | 2/2010 | Bodner et al. |
| 7,678,145 B2 | 3/2010 | Vidlund et al. |
| 7,753,949 B2 | 7/2010 | Lamphere et al. |
| 7,785,366 B2 | 8/2010 | Maurer et al. |
| 8,092,525 B2 | 1/2012 | Eliasen et al. |
| 8,216,302 B2 | 7/2012 | Wilson et al. |
| 2001/0007956 A1 | 7/2001 | Letac et al. |
| 2001/0010017 A1 | 7/2001 | Cribier et al. |
| 2002/0042651 A1 | 4/2002 | Liddicoat et al. |
| 2002/0058995 A1 | 5/2002 | Stevens |
| 2002/0077566 A1 | 6/2002 | Laroya et al. |
| 2002/0081553 A1 | 6/2002 | Tramonte |
| 2002/0183838 A1 | 12/2002 | Liddicoat et al. |
| 2002/0188170 A1 | 12/2002 | Santamore et al. |
| 2003/0033009 A1 | 2/2003 | Gabbay |
| 2003/0040792 A1 | 2/2003 | Gabbay |
| 2003/0105519 A1 | 6/2003 | Fasol et al. |
| 2003/0130731 A1 | 7/2003 | Vidlund et al. |
| 2003/0139751 A1 | 7/2003 | Evans et al. |
| 2003/0144574 A1 | 7/2003 | Heilman et al. |
| 2003/0181945 A1 | 9/2003 | Opolski et al. |
| 2003/0199975 A1 | 10/2003 | Gabbay |
| 2003/0208203 A1 | 11/2003 | Lim et al. |
| 2003/0212453 A1 | 11/2003 | Mathis et al. |
| 2004/0034366 A1 | 2/2004 | van der Burg et al. |
| 2004/0044402 A1 | 3/2004 | Jung et al. |
| 2004/0088047 A1 | 5/2004 | Spence et al. |
| 2004/0106989 A1 | 6/2004 | Wilson et al. |
| 2004/0122512 A1 | 6/2004 | Navia et al. |
| 2004/0127981 A1 | 7/2004 | Rahdert et al. |
| 2004/0127983 A1 | 7/2004 | Mortier et al. |
| 2004/0148020 A1 | 7/2004 | Vidlund et al. |
| 2004/0181256 A1 | 9/2004 | Glaser |
| 2004/0210304 A1 | 10/2004 | Sequin et al. |
| 2004/0210307 A1 | 10/2004 | Khairkhahan |
| 2004/0225353 A1 | 11/2004 | McGuckin, Jr. et al. |
| 2004/0225354 A1 | 11/2004 | Allen et al. |
| 2004/0243229 A1 | 12/2004 | Vidlund et al. |
| 2005/0021056 A1 | 1/2005 | St. Goar et al. |
| 2005/0033446 A1 | 2/2005 | Deem et al. |
| 2005/0038508 A1 | 2/2005 | Gabbay |
| 2005/0038509 A1 | 2/2005 | Ashe |
| 2005/0065591 A1 | 3/2005 | Moberg et al. |
| 2005/0070999 A1 | 3/2005 | Spence |
| 2005/0075727 A1 | 4/2005 | Wheatley |
| 2005/0090824 A1 | 4/2005 | Shluzas et al. |
| 2005/0131451 A1 | 6/2005 | Kleshinski et al. |
| 2005/0159810 A1 | 7/2005 | Filsoufi |
| 2005/0222488 A1 | 10/2005 | Chang et al. |
| 2005/0288786 A1 | 12/2005 | Chanduszko |
| 2006/0025855 A1 | 2/2006 | Lashinski et al. |
| 2006/0058871 A1 | 3/2006 | Zakay et al. |
| 2006/0084943 A1 | 4/2006 | Rosenman et al. |
| 2006/0129025 A1 | 6/2006 | Levine et al. |
| 2006/0149368 A1 | 7/2006 | Spence |
| 2006/0155326 A1 | 7/2006 | Aranyi |
| 2006/0178700 A1 | 8/2006 | Quinn |
| 2006/0195012 A1 | 8/2006 | Mortier et al. |

(56) References Cited

U.S. PATENT DOCUMENTS

| | | |
|---|---|---|
| 2006/0195185 A1 | 8/2006 | Lane et al. |
| 2006/0199995 A1 | 9/2006 | Vijay |
| 2006/0229708 A1 | 10/2006 | Powell et al. |
| 2006/0241745 A1 | 10/2006 | Solem |
| 2006/0253072 A1 | 11/2006 | Pai et al. |
| 2006/0293698 A1 | 12/2006 | Douk |
| 2007/0049980 A1 | 3/2007 | Zielinski et al. |
| 2007/0093890 A1 | 4/2007 | Eliasen et al. |
| 2007/0118151 A1 | 5/2007 | Davidson |
| 2007/0167981 A1 | 7/2007 | Opolski et al. |
| 2007/0185571 A1 | 8/2007 | Kapadia et al. |
| 2007/0198050 A1 | 8/2007 | Ravenscroft et al. |
| 2007/0198082 A1 | 8/2007 | Kapadia et al. |
| 2007/0213578 A1 | 9/2007 | Khairkhahan et al. |
| 2007/0232981 A1 | 10/2007 | Ravenscroft et al. |
| 2007/0239154 A1 | 10/2007 | Shaolian et al. |
| 2007/0255399 A1 | 11/2007 | Eliasen et al. |
| 2007/0265700 A1 | 11/2007 | Eliasen et al. |
| 2007/0282429 A1 | 12/2007 | Hauser et al. |
| 2007/0293943 A1 | 12/2007 | Quinn |
| 2008/0125860 A1 | 5/2008 | Webler et al. |
| 2008/0125861 A1 | 5/2008 | Webler et al. |
| 2008/0183105 A1 | 7/2008 | Greenhalgh et al. |
| 2008/0195200 A1 | 8/2008 | Vidlund et al. |
| 2008/0288061 A1 | 11/2008 | Maurer et al. |
| 2009/0043382 A1 | 2/2009 | Maurer et al. |
| 2009/0048668 A1 | 2/2009 | Wilson et al. |
| 2009/0105814 A1 | 4/2009 | Groothuis et al. |
| 2009/0131849 A1 | 5/2009 | Maurer et al. |
| 2009/0131880 A1 | 5/2009 | Speziali et al. |
| 2009/0132033 A1 | 5/2009 | Maurer et al. |
| 2009/0163934 A1 | 6/2009 | Raschdorf, Jr. et al. |
| 2009/0240326 A1 | 9/2009 | Wilson et al. |
| 2010/0324668 A1 | 12/2010 | Maurer et al. |
| 2012/0143320 A1 | 6/2012 | Eliasen et al. |

FOREIGN PATENT DOCUMENTS

| | | |
|---|---|---|
| GB | 1264472 | 2/1972 |
| GB | 1268484 | 3/1972 |
| GB | 1388064 | 3/1975 |
| WO | 03/049619 | 6/2003 |
| WO | WO2006032051 | 3/2006 |
| WO | 2006/064490 A1 | 6/2006 |
| WO | 2006091597 | 8/2006 |
| WO | 2006/111391 | 10/2006 |
| WO | 2006127509 | 11/2006 |
| WO | 2007064810 | 6/2007 |
| WO | 2007078772 | 7/2007 |
| WO | 2007100409 | 9/2007 |
| WO | 2007/140470 A2 | 12/2007 |
| WO | 2008079828 | 7/2008 |
| WO | 2009053952 A2 | 4/2009 |

OTHER PUBLICATIONS

Preliminary Report on Patentability dated Nov. 1, 2011 issued in PCT Patent Application No. PCT/US2010/032764, 4 pages.
U.S. Office Action dated Nov. 3, 2011 issued in U.S. Appl. No. 12/872,228, 8 pages.
Notice of Allowance dated Dec. 14, 2011 issued in U.S. Appl. No. 12/431,399, 12 pages.
U.S. Office Action dated Dec. 21, 2011, issued in U.S. Appl. No. 11/748,121, 9 pages.
U.S. Office Action dated Jan. 18, 2012 issued in U.S. Appl. No. 11/940,724, 10 pages.
U.S. Office Action dated Dec. 15, 2009 issued in U.S. Appl. No. 11/258,828, 12 pages.
U.S. Office Action dated Jan. 8, 2010 issued in U.S. Appl. No. 11/748,147, 63 pages.
U.S. Office Action dated Jan. 14, 2010 issued in U.S. Appl. No. 11/940,674, 59 pages.
U.S. Office Action dated Jan. 25, 2010 issued in U.S. Appl. No. 11/748,121, 9 pages.
U.S. Office Action dated Feb. 4, 2010 issued in U.S. Appl. No. 11/748,138, 58 pages.
Glenn et al., "The Surgical Treatment of Mitral Insufficiency with Particular Reference to the Application of a Vertically Suspended Graft" Jul. 1956 (pp. 59-77).
Glover, et al., "The Fate of Intracardiac Pericardial Grafts as Applied to the Closure of Septal Defects and to the Relief of Mitral Insufficiency" 1952 (pp. 178-185).
Harken et al., "The Surgical Correction of Mitral Insufficienty" Surgical Forum 1954 (pp. 4-7).
Harken et al, "The Surgical Correction of Mitral Insufficiency" The Journal of Thoracic Surgery 1954 (pp. 604-627).
Henderson et al., "The Surgical Treatment of Mitral Insufficiency" Jun. 1953 (pp. 858-868).
International Search and Written Opinion mailed May 11, 2007 filed in corresponding PCT patent application PCT/US06/39011 (8 pages).
Johns et al., Mitral Insufficiency: the Experimental Use of a Mobile Polyvinyl sponge Prosthesis: Sep. 1954 (pp. 335-341).
Moore, et al., "Unsuitability of Transventricular Autogenous Slings for Diminishing Valvular Insufficiency" Feb. 1953 (pp. 173-182).
"PVA Datasheet", www.sponge-pva.com/data.htm, Dec. 20, 2006, 2 pages.
"PVA Sponge W (wet) & D (dry)", Ceiba Technologies, http://www.ceibatech.com/PVASpongeW&D.htm, Dec. 20, 2007 5 pages.
Sakakibara, "A Surgical Approach to the Correction of Mitral Insufficienty" Aug. 1955 (pp. 196-203).
SPI-Chem™ Vinylec® (Formvar®) Resins, http://www.2spi.com/catalog/submat/formvar-resins.shtml, Dec. 20, 2006, 5 pages.
Trippel et al, "Reinforced Ivalon Sponge as an Aortic Prosthesis", Annals of Surgery, Feb. 1960, vol. 151, No. 2, pp. 216-224.
"Vinylec® Resins", http://www.2spi.com/catalog/submat/vinylec-physical.html, Dec. 20, 2006, 1 page.
U.S. Office Action dated Jun. 20, 2012 issued in U.S. Appl. No. 11/940,694, 9 pages.
U.S. Office Action dated Jun. 21, 2012 issued in U.S. Appl. No. 11/748,147, 29 pages.
Notice of Allowance dated Jul. 20, 2012 issued in U.S. Appl. No. 11/748,121, 10 pages.
Eisenhauer et al., Closure of Prosthetic Paravalvular Mitral Regurgitation With the Gianturco-Grifka Vascular Occlusion Device, Catheterization and Cardiovascular Interventions, 2001, 5 pages,vol. 54.
Hourihan et al., Transcatheter Umbrella Closure of Valvular and Paravalvular Leaks, American College of Cardiology, Nov. 15, 1992, 7 pages, vol. 20, No. 6.
Moscucci et al., Coil Embolization of a Periprosthetic Mitral Valve Leak Associated With Severe Hemolytic Anemia, Images in Cardiovascular Medicine, American Heart Association, Inc., 2001, 2 pages, vol. 104.
Rashkind et al. Nonsurgical closure of patent ductus arteriosus: clinical application of the Rashkind PDA Occluder System, Therapy and Prevention—Congenital Heart Disease, Mar. 1987, 10 pages, vol. 75, No. 3.
Ryhänen et al., Invivo biocompatibility evaluation of nickel-titanium shape memory metal alloy: Muscle and perineural tissue responses and encapsule membrane thickness, Muscle and Perineural Tissue Response to Nitinol, Received Aug. 11, 1997; accepted Jan. 19, 1998, 8 pages.
International Search Report and Written Opinion dated Jan. 16, 2009 issued in PCT Application No. PCT/US08/83497, 10 pages.
Extended European search report dated Nov. 30, 2010 issued in European Patent Application No. 08850467.5, 6 pages.
Extended European search report dated Nov. 30, 2010 issued in European Patent Application No. 08755418.4, 7 pages.
Extended European search report dated Nov. 30, 2010 issued in European Patent Application No. 08849442.2, 6 pages.
International Preliminary Report on Patentability dated Jan. 31, 2012 issued in PCT Patent Application No. PCT/US2010/043360, 7 pages.
U.S. Office Action dated Feb. 15, 2012 issued in U.S. Appl. No. 11/940,694, 9 pages.
U.S. Notice of Allowance dated Mar. 8, 2012 issued in U.S. Appl. No. 12/872,228, 7 pages.

(56) References Cited

OTHER PUBLICATIONS

U.S. Office Action dated Jul. 8, 2009 issued in U.S. Appl. No. 11/258,828, 7 pages.
International Search Report and Written Opinion dated Aug. 11, 2009 issued in PCT Application No. PCT/US2009/046995, 11 pages.
U.S. Office Action dated Sep. 29, 2009 issued in U.S. Appl. No. 12/209,686, 9 pages.
Balzer et al., Real-time transesophageal three-dimensional echocardiography for guidance of percutaneous cardiac interventions: first experience, Clinical Research in Cardiology, May 29, 2008, 565-574, vol. 97, No. 9.
Carlson et al., Lead Perforation: Incidence in Registries, Pace Industry Viewpoint, Jan. 2008, 13-15, vol. 31.
Clinical Trials.gov, Comparing the Effectiveness of a Mitral Valve Repair Procedure in Combination With Coronary Artery Bypass Grafting (CABG) Versus CABG Alone in People with Moderate Ischemic Mitral Regurgitation, http://clinicaltrials.gov/ct2/show/record/NCT00806988?term=mitral+repair&rank=7, Feb. 24, 2009, 1-3.
Clinical Trials.gov, Safety and Efficacy Study of the PTMA Device to Reduce Mitral Valve Regurgitation in Patients With Heart Failure (PTOLEMY2Canada), http://clinicaltrials.gov/ct2/show/study/NCT00815386?term=Viacor&rank=3, 1-3.
Clinical Trials.gov, Study of Safety and Efficacy of the Percutaneous Reduction of Mitral Valve Regurgitation in Heart Failure Patients (PTOLEMY-2), http://clinicaltrials.gov/ct2/show/NCT00787293?term=Viacor&rank=5, 1-2.
Cohen, Trans-Septal Technique for Tandemheart Insertion, Lenox Hill Heart and Vascular Institute of New York, Barcelona May 22-May 25, 2007, 18 pages.
Corbisiero et al., Does Size Really Matter? A Comparison of the Riata Lead Family Based on Size and Its Relation to Performance, Pace, Jun. 2008, vol. 31, 722-726.
Criber et al., Treatment of Calcific Aortic Stenosis With the Percutaneous Heart Valve—Mid-Term Follow-Up From the Initial Feasibility Studies: The French Experience, Journal of the American College of Cardiology, Mar. 21, 2006, vol. 47, No. 6, 1241-1223.
Danik et al., Timing of delayed perforation with the St. Jude Riata lead: A single-center experience and a review of the literature, Heart Rhythm Society, Dec. 2008, vol. 5, No. 12, 1667-1672.
Del Valle-Fern ández et al., Transcatheter heart valves for the treatment of aortic stenosis: state-of-the-art, Minerva Cardioangiologica, Oct. 2008, vol. 56, No. 5, 543-556.
Douthitt, Cardiac Dimensions® Inc. Receives CE Mark for CARILLON™Mitral Contour System™, Cardiac Dimensions—News, htpp://www.cardiacdimensions.com/usa/press-release-2-4-09.html, downloaded Feb. 24, 2009, 1-2.
Dvorin, Endovalve Inc., Pioneering percutaneous mitral valve replacement., Start-Up Windhover's Review of Emerging Medical Ventures, Jun./Jul. 2006, vol. 11, No. 7, 1-2.
Eltchaninoff, Clinical results of percutaneous aortic valve implantation, Euro PCR07, Cribier-Edwards, 30 pages.
Evalve reports 1st MitraClip treatments in the Netherlands, Medical Device Daily, Feb. 19, 2009, vol. 13, No. 32, 2 pages.
A first for MiCardia's Dynoplasty, Medical Device Daily, Feb. 19, 2009, vol. 13, No. 32, 1 page.
Fitts et al., Fluoroscopy-Guided Femoral Artery Puncture Reduces the Risk of PCI-Related Vascular Complications, Journal of Interventional Cardiology, vol. 21, No. 3, 2008, 273-278.
Gelsomino et al., Left ventricular diastolic function after restrictive mitral ring annuloplasty in chronic ischemic mitral regurgitation and its predictive value on outcome and recurrence of regurgitation, International Journal of Cardiology, vol. 132, 2009, 419-428.
Geyfman et al., Cardiac Tamponade as Complication of Active-Fixation Atrial Lead Perforations: Proposed Mechanism and Management Algorithm, PACE, Apr. 2007, vol. 30, 498-501.
Gorman et al., Surgical Therapy for Mitral Regurgitation: The Key to Preventing Heart Failure?, Prevention of Heart Failure After Myocardial Infarction, 2008, 211-215.

Harper, Evalve Announces Enrollment Completion of the Everest Randomized Study, http://www.evalveinc.com/europe/press/17.html, downloaded Feb. 24, 2009, 1-3.
Harper, Two-Year Follow-Up Data Demonstrates Preservation of Adequate Mitral Valve Area in Patients Treated with the MitraClip®-system, http://www.evalveinc.com/europe/press/21.html, downloaded Feb. 24, 2009, 1-3.
Hung et al., 3D Echocardiography: A Review of the Current Status and Future Directions, ASE Position Paper, Journal of the American Society of Echocardiography, Mar. 2007, 213-233.
Hung et al., Mechanism of Dynamic Regurgitant Orifice Area Variation of Functional Mitral Regurgitation—Physiologic Insights From the Proximal Flow Convergence Technique, Journal of the American College of Cardiology, Feb. 1999, vol. 33, No. 2, 538-545.
Hung et al., A Novel Approach for Reducing Ischemic Mitral Regurgitation by Injection of a Polymer of Reverse Remodel and Reposition Displaced Papillary Muscles, Circulation—Journal of the American Heart Association, Sep. 30, 2008, Downloaded from circ.ahajournals.org at National Insthealth Lib on Feb. 25, 2009, S262-S269.
Hytowitz, First U.S. Patients Enrolled In The Realism Continued Access Study, evalve, http://www.evalveinc.com/europe/press/22/html, downloaded Feb. 24, 2009, 2 pages.
International Search Report and Written Opinion dated Feb. 25, 2009 issued in PCT Application No. PCT/US08/83570, 13 pages.
International Search Report and Written Opinion dated Apr. 2, 2009 issued in PCT Application No. PCT/US08/83574, 8 pages.
Jilaihawi et al., Percutaneous Aortic Valve Replacement in Patients with Challenging Aortoiliofemoral Access, Catheterization and Cardiovascular Interventions, 2008, vol. 72, 885-890.
Jovin et al., Atrial Fibrillation and Mitral Valve Repair, Pace, Aug. 2008, vol. 31, 1057-1063.
Kahlert et al., Direct Assessment of Size and Shape of Noncircular Vena Contracta Area in Functional Versus Organic Mitral Regurgitation Using Real-Time Three-Dimensional Echocardiography, Valvular Heart Disease, Journal of the American Society of Echocardiography, Aug. 2008, vol. 21, No. 8, 912-921.
Kempfert et al., Minimally invasive off-pump valve-in-a-valve implantation: the atrial transcatheter approach for re-operative mitral valve replacement, European Heart Journal, 2008, vol. 29, 2382-2387.
Kerensky, Complications of Cardiac Catheterization and Strategies to Reduce Risks, Diagnostic and Therapeutic Cardiac Catheterization—Third Edition—Chapter 8, 1998, 17 pages.
Kodali et al., Transcatheter Valve Repair and Replacement, Downloaded from arjournals.annualreviews.org by National Institute of Health Library on Feb. 25, 2009, 14 pages.
Kwan et al., Geometric Differences of the Mitral Apparatus Between Ischemic and Dilated Cardiomyopathy With Significant Mitral Regurgitation—Real-Time Three-Dimensional Echocardiography Study, Circulation, Mar. 4, 2003, 1135-1140.
Leung et al., Percutaneous Mitral Valve Repair—An overview of the current devices and techniques, Coronory/Cardiac Interventions—Endovascular Today, Oct. 2006, 26-33.
Levine et al., Mechanistic Insights into Functional Mitral Regurgitation, Valvular Heart Disease, 2009, 125-129.
Little et al., Three-Dimensional Ultrasound Imaging Model of Mitral Valve Regurgitation: Design and Evaluation, Ultrasound in Medicine and Biology, 2008, vol. 34, No. 4, 647-654.
Llaneras et al., Large Animal Model of Ischemic Mitral Regurgitation, The Society of Thoracic Surgeons—Ischemic Mitral Insufficiency, 1994, vol. 57, 432-439.
Magne et al., Ischemic Mitral Regurgitation: A Complex Multifaceted Disease, Cardiology, 2009, vol. 112, 244-259.
McClure et al., Early and late outcomes in minimally invasive mitral valve repair: An eleven-year experience in 707 patients, Acquired Cardiovascular Disease, The Journal of Thoracic and Cardiovascular Surgery, Jan. 2009, vol. 137, No. 1, 70-75.
Modi et al., Minimally invasive mitral valve surgery: a systematic review and meta-analysis, European Journal of Cardio-Thoracic Surgery, 2008, vol. 34, 943-952.

(56) References Cited

OTHER PUBLICATIONS

Myers, Jr., et al., Color Doppler Velocity Accuracy Proximal to Regurgitant Orifices: Influence of Orifice Aspect Ratio, Ultrasound in Medicine and Biology, 1999, vol. 25, No. 5, 771-792.
Ning et al., Live three-dimensional transesophageal echocardiography in mitral valve surgery, Chinese Medical Journal, 2008, vol. 121, No. 20, 2037-2041.
Nötzold et al., Microemboli in aortic valve replacement, Future Drugs Ltd, Expert Rev. Cardiovasc. Ther., vol. 4, No. 6, 2006, 853-859.
Onundarson et al., Warfarin anticoagulation intensity in specialist-based and in computer-assisted dosing practice, International Journal of Laboratory Hematology, 2008, vol. 30, 382-389.
Otsuji et al., Insights From Three-Dimensional Echocardiography Into the Mechanism of Functional Mitral Regurgitation—Direct In Vivo Demonstration of Altered Leaflet Tethering Geometry, Circulation, Sep. 16, 1997, vol. 96, No. 6, 1999-2008.
Fukuda et al., Maintenance of Geometric Alterations Associated with Percutaneous Mitral Valve Repair: Real-Time Three-Dimensional Echocardiographic Assessment in an Ovine Model, J. Heart Valve Dis, May 2008, vol. 17, No. 3, 276-282.
Pai et al., Effect of Atrial Fibrillation on the Dynamics of Mitral Annular Area, J. Heart Valve Dis., Jan. 2003, vol. 12, No. 1, 31-37.
Palacios et al., Safety and Feasibility of Acute Percutaneous Septal Sinus Shortening: First-In-Human Experience, Catheterization and Cardiovascular Interventions, 2007, vol. 69, 513-518.
Paniagua et al., First Human Case of Retrograde Transcatheter Implantation of an Aortic Valve Prosthesis, Texas Heart Institute Journal, Transcatheter Aortic Valve Prosthesis, 2005, vol. 32, No. 3, 393-398.
Rodés-Cabau et al., Feasibility and Initial Results of Percutaneous Aortic Valve Implantation Including Selection of the Transfemoral or Transapical Approach in Patients With Severe Aortic Stenosis, The American Journal of Cardiology, 2008, 1240-1246.
Satpathy et al., Delayed Defibrillator Lead Perforation: An Increasing Phenomenon, Pace, Jan. 2008, vol. 31, 10-12.
Schofer, Percutaneous MVR: Clinical Evaluation—The Carillon Experience, EuroPCR 2007, Barcelona, Spain, May 22-25, 2007, 35 pages.
Schwammenthal et al., Dynamics of Mitral Regurgitant Flow and Orifice Area—Physiologic Application of the Proximal Flow Convergence Method: Clinical Data and Experimental Testing, Circulation, Jul. 1994, vol. 90, No. 1, 307-322.
Spencer, Viacor, Inc. Announces First Patient Treated in PTOLEMY-2 Study, http://www.viacorinc.com/viacor_news.html, Nov. 14, 2008, downloaded Feb. 24, 2009, 2 pages.
Sterliński et al., Subacute cardiac perforations associated with active fixation leads, Clinical Research Leads and Lead Extraction, Europace, 2009, vol. 11, 206-212.
Turakhia et al., Rates and severity of perforation from implantable cardioverter-defibrillator leads: A 4-year study, J Interv Card Electrophysiol, 2009, vol. 24, 47-52.
Vahanian, The Cardiologist's Perspective on the Future of Percutaneous Mitral Valve Repair, Euro PCR07, 53 pages.
Vahanian, Coronary Sinus and Direct Annuloplasty Percutaneous Mitral Valve Repair, Innovations in Cardiovascular Interventions, Dec. 7-9, 2008, Tel-Aviv, Israel, 45 pages.
Vahanian, Edwards MONARC system—Evolution Interim Results, 31 pages.
Vahanian, Overview on Percutaneous Mitral Valve Technology, Euro PCR07, Transcatheter Valve Symposium, Barcelona, May 22-25, 2007, 29 pages.
Van Gelder et al., Diagnosis and Management of Inadvertently Placed Pacing and ICD Leads in the Left Ventricle: A Multicenter Experience and Review of the Literature, Pace, May 2000, vol. 23, 877-883.
Vranckx et al., The TandemHeart®, percutaneous transseptal left ventricular assist device: a safeguard in high-risk percutaneous coronary interventions. The six-year Rotterdam experience, Clinical research EuroInterv., 2008, vol. 4, 331-337.
Wolf et al., Solid and gaseous cerebral micorembolization after biologic and mechanical aortic valve replacement: Investigation with multirange and multifrequency transcranial Doppler ultrasound, The Journal of Thoracic and Cardiovascular Surgery, Mar. 2008, vol. 135, No. 3, 512-520.
Xiangming et al., In Vivo Characterization of Attachment Safety Between Cardiac Pacing Lead and Canine Heart Muscle, Acta Mechanica Solida Sinica, Sep. 2007, vol. 20, No. 3, 189-197.
Yamaura et al., Geometrical Demonstration and Three-Dimensional Quantitative Analysis of the Mitral Valve With Real-Time Three-Dimensional Echocardiography: Novel Anatomical Image Creation System, J Echocardiogr, 2004, vol. 2, No. 4, 99-104.
Yosefy et al., Proximal Flow Convergence Region as Assessed by Real-time 3-Dimensional Echocardiography: Challenging the Hemispheric Assumption, Journal of the American Society of Echocardiography, Apr. 2007, vol., No. 4, 389-396.
U.S. Office Action dated Jun. 2, 2010 issued in U.S. Appl. No. 12/209,686, 15 pages.
U.S. Office Action dated Jun. 28, 2010 issued in U.S. Appl. No. 11/258,828, 14 pages.
Notice of Allowance dated Jul. 1, 2010 issued in U.S. Appl. No. 11/940,674, 6 pages.
International Search Report and Written Opinion dated Jul. 6, 2010 issued in PCT Patent Application No. PCT/US2010/032764, 9 pages.
U.S. Office Action dated Jul. 20, 2010 issued in U.S. Appl. No. 11/748,147, 15 pages.
Ryhänen et al., In vivo biocompatibility evaluation of nickel-titanium shape memory metal alloy: Muscle and perineural tissue responses and encapsule membrane thickness, Muscle and Perineural Tissue Response to Nitinol, Jan. 19, 1998, pp. 481-488.
Extended European Search Report dated Dec. 1, 2010 issued in European Patent Application No. 08755426.7, 6 pages.
Extended European Search Report dated Dec. 14, 2010 issued in European Patent Application No. 06816336.9, 7 pages.
U.S. Office Action dated Mar. 21, 2011 issued in U.S. Appl. No. 11/258,828, 22 pages.
U.S. Office Action dated Mar. 29, 2011 issued in U.S. Appl. No. 11/748,121, 14 pages.
U.S. Office Action dated Apr. 4, 2011 issued in U.S. Appl. No. 11/940,724, 65 pages.
European Examination Report dated Aug. 4, 2011 issued in European Patent No. 06 816 336.9, 3 pages.
U.S. Office Action dated Aug. 29, 2011 issued in U.S. Appl. No. 11/940,694, 11 pages.
European Examination Report dated Aug. 11, 2011 issued in European Patent No. 08 755 418.4, 3 pages.
Kerensky, Complications of Cardiac Catheterization and Strategies to Reduce Risks, Diagnostic and Therapeutic Cardiac Catheterization, 1998, Chapter 8, 91-105.
Koertke et al., INR Self-Management Permits Lower Anticoagulation Levels After Mechanical Heart Valve Replacement, downloaded from circ.ahajournals.org, Aug. 26, 2008, II-75-II-78.
Kratz et al., St. Jude Prosthesis for Aortic and Mitral Valve Replacement: A Ten-Year Experience, The Society of Thoracic Surgeons, 1993, 462-8, 56.
Kron et al., Surgical Relocation of the Posterior Papillary Muscle in Chronic Ischemic Mitral Regurgitation, The Society of Thoracic Surgeons, 2002, 600-1, 74.
Kuwahara et al., Mechanism of Recurrent/Persistent Ischemic/Functional Mitral Regurgitation in the Chronic Phase After Surgical Annuloplasty—Importance of Augmented Posterior Leaflet Tethering, Circulation, Jul. 4, 2006, I-529-I-534.
Laskey et al., Multivariable Model for Prediction of Risk of Significant Complication During Diagnostic Cardiac Catheterization, Catheterization and Cardiovascular Diagnosis, 1993, 185-190, 30.
Lee et al., Mitral Valve Reconstruction: Experience Related to Early and Late Mortality and Reoperation, J Heart Valve Dis, Nov. 2005, 715-721, vol. 14, No. 6.
Liddicoat et al., Percutaneous Mitral Valve Repair: A Feasibility Study in an Ovine Model of Acute Ischemic Mitral Regurgitation, Catheterization and Cardiovascular Interventions, 2003, 410-416, 60.

(56) References Cited

OTHER PUBLICATIONS

Lim et al., Percutaneous Transthoracic Ventricular Puncture for Diagnostic and Interventional Catheterization, Catheterization and Cardiovascular Interventions, 2008, 915-918, 71.
Lin et al., Severe Symptomatic Tricuspid Valve Regurgitation Due to Permanent Pacemaker or Implantable Cardioverter-Defibrillator Leads, Journal of the American College of Cardiology, May 17, 2005, 1672-5, vol. 45, No. 10.
Lozonschi et al., Transapical Mitral Valved Stent Implantation, The Society of Thoracic Surgeons, 2008, 745-8, 86.
Mack, Percutaneous Therapies For Mitral Regurgitation: Where Do We Stand and Where Are We Going? Do Current Devices Really Represent a Step Forward Compared to Surgery?, 2007 Heart Valve Summit, Jun. 7, 2007, 59 pages.
Maleki et al., Intracardiac Ultrasound Detection of Thrombus on Transseptal Sheath: Incidence, Treatment, and Prevention, Journal of Cardiovascular Electrophysiology, Jun. 2005, 561-565, vol. 16, No. 6.
Maniu et al., Acute and Chronic Reduction of Functional Mitral Regurgitation in Experimental Heart Failure by Percutaneous Mitral Annuloplasty, Journal of the American College of Cardiology, Oct. 19, 2004, 1652-61, vol. 44, No. 8.
McGee et al., Recurrent mitral regurgitation after annuloplasty for functional ischemic mitral regurgitation, Surgery for Acquired Cardiovascular Disease, The Journal of Thoracic and Cardiovascular Surgery, Dec. 2004, 916-924.e4, vol. 128, No. 6.
Mehra et al., Surgery for Severe Mitral Regurgitation and Left Ventricular Failure: What Do We Really Know?, Journal of Cardiac Failure, Mar. 2008, 145-150. vol. 14, No. 2.
Menicanti et al., Functional Ischemic Mitral Regurgitation in Anterior Ventricular Remodeling: Results of Surgical Ventricular Restoration with and Without Mitral Repair, Heart Failure Reviews, 2004, 317-327, 9.
Messas et al., Efficacy of Chordal Cutting to Relieve Chronic Persistent Ischemic Mitral Regurgitation, Circulation, Sep. 9, 2003, II-111-II-115.
Meurin et al., Thromboembolic events early after mitral valve repair: Incidence and predictive factors, International Journal of Cardiology, 2008, 45-52, 126.
Mirable et al., What are the characteristics of patients with severe, symptomatic, mitral regurgitation who are denied surgery?, The European Society of Cardiology, 2007, 1358-65, 28.
Mitchell et al., Complications, Cardiac catheterization and coronary intervention, Chapter 9, 2008, 238-270.
Mishra et al., Coapsys Mitral Annuloplasty for Chronic Functional Ischemic Mitral Regurgitation: 1-Year Results, The Society of Thoracic Surgeons, 2006, 42-46, 81.
Morgan et al., Left Heart Catheterization by Direct Ventricular Puncture: Withstanding the Test of Time, Catheterization and Cardiovascular Diagnosis, 1989, 87-90, 16.
Murday et al., A Prospective Controlled Trial of St. Jude Versus Starr Edwards Aortic and Mitral Valve Prostheses, The Society of Thoracic Surgeons, 2003, 66-74, 76.
Nifong et al., Robotic mitral valve surgery: A United States multicenter trial, The Journal of Thoracic and Cardiovascular Surgery, Jun. 2005, 1395-1404, vol. 129, No. 6.
Noto et al., Cardiac Catheterization 1990: A Report of the Registry of the Society for Cardiac Angiography and Interventions (SCA&I), Catheterization and Cardiovascular Diagnosis, 1991, 75-83, 24.
Ohlow et al., Incidence and outcome of femoral vascular complications among 18,165 patients undergoing cardiac catheterisation, International Journal of Cardiology, 2008, 1-6.
Piazza et al., Transcatheter Mitral Valve Repair for Functional Mitral Regurgitation: Coronary Sinus Approach, Journal of Interventional Cardiology, 2007, 495-508, vol. 20, No. 6.
Pedersen et al., iCoapsys Mitral Valve Repair System: Percutaneous Implantation in an Animal Model, Catheterization and Cardiovascular Interventions, 2008, 125-131, 72.
Prifti et al., Ischemic Mitral Valve Regurgitation Grade II-III: Correction in Patients with Impaired Left Ventricular Function undergoing Simultaneous Coronary Revascularization, J Heart Valve Dis, Nov. 2001, 754-762, vol. 10, No. 6.
Richardson et al., Is a port-access mitral valve repair superior to the sternotomy approach in accelerating postoperative recovery?, Interactive CardioVascular and Thoracic Surgery, Downloaded from icvts.ctsnetjournals.org, Aug. 26, 2008, 670-683, 7.
Ruiz, New Percutaneous Approaches for Mitral Regurgitation, Lenox Hill Heart and Vascular Institute of New York, May 13-16, 2008, 26 pages.
Rumel et al., Section On Cardiovascular Diseases—The Correction of Mitral Insufficiency With a Trans-Valvular Polyvinyl Formalinized Plastic (Ivalon) Sponge Prosthesis, American College of Chest Physicians, Apr. 1958, Downloaded from chestjournal.org, Jul. 23, 2008, 401-413.
Seeburger et al., Minimal invasive mitral valve repair for mitral regurgitation: results of 1339 consecutive patients, European Journal of Cardio-thoracic Surgery, 2008, 1-6.
Southard et al., Current Catheter-Based Treatments of Functional Mitral Regurgitation, Cardiac Interventions Today, Jun. 2007, 41-44.
Svensson et al., United States Feasibility Study of Transcatheter Insertion of a Stented Aortic Valve by the Left Ventricular Apex, The Society of Thoracic Surgeons, 2008, 46-55, 86.
Toledano et al., Mitral regurgitation: Determinants for referral for cardiac surgery by Canadian cardiologists, Can J. Cardiol, Mar. 1, 2007, 209-214, vol. 23, No. 3.
Tops et al., Percutaneous Valve Procedures: An Update, Curr Probl Cardiol, Aug. 2008, 417-426.
Walther et al., Transapical minimally invasive aortic valve implantation; the initial 50 patients, European Journal of Cardio-thoracic Surgery, 2008, 983-988, 33.
Webb et al., Percutaneous Mitral Annuloplasty With the MONARC System: Preliminary Results From the Evolution Trial, TCT-103, The American Journal of Cardiology, Oct. 22-27, 2006, 49M.
Webb et al., Percutaneous Transvenous Mitral Annuloplasty—Initial Human Experience with Device Implantation in the Coronary Sinus, downloaded from circ.ahajournals.org, Aug. 26, 2008, 851-855.
Webster et al., Impact of transvenous ventricular pacing leads on tricuspid regurgitation in pediatric and congenital heart disease patients, J Interv Card Electrophysiol, 2008, 65-68, 21.
Ye et al., Six-month outcome of transapical transcatheter aortic valve implantation in the initial seven patients, European Journal of Cardio-thoracic Surgery, 2007, 16-21, 31.
Yoshida, et al., Assessment of Left-to-Right Atrial Shunting After Percutaneous Mitral Valvuloplasty by Transesophageal Color Doppler Flow-Mapping, Circulation, Dec. 1989, 1521-1526, vol. 80, No. 6.
Zhou et al., Thromboembolic Complications of Cardiac Radiofrequency Catheter Ablation: A Review of the Reported Incidence, Pathogenesis and Current Research Directions, Journal of Cardiovascular Electrophysiology, Apr. 1999, 611-620, vol. 10, No. 4.
Bailey et al, "Surgical Repair of Mitral Insufficiency" Feb. 1951 (pp. 125-137).
Bailey et al, "Closed Intracardiac Tactile Surgery" Jul. 1952 (pp. 1-24).
Bailey et al., "The Surgical Correction of Mitral Insufficiency by the Use of Pericardial Grafts" Dec. 1954 (pp. 551-627).
Benichoux et al., "A Method of Surgical Correction of Mitral Insufficiency" 1955 (pp. 148-158).
Blalock, "A Consideration of Some of the Problems in Cardiovascular Surgery" Jun. 1951 (pp. 543-571).
Borrie, "Mitral Insufficiency: Experimental Circular Suture Around the Artioventricular Ring" 1955 (pp. 687-697).
Carter et al. "Surgical Treatment of Mitral Insufficiency" 1953 (pp. 574-583).
European Search Report dated Jul. 12, 1984 cited in EP0125393.
"French catheter scale chart" http://en.wikipedia.org/wiki/French_catheter_scale_chart, Dec. 20, 2006, 1 page.
"General Physical Properties of PVA Sponge (values are not guaranteed)", Ceiba Technologies, http://www.ceibatech.com/PVASpongeDate.htm, Dec. 20, 2006 3 pages.
Glenn et al., "The Implantation of a Vascularized Graft in the Chambers of the Heart" 1954 (pp. 5-11).

(56) References Cited

OTHER PUBLICATIONS

Glenn et al, "The Surgical Treatment of Mitral Insufficiency: the Fate of Vascularized Transchamber Intracardiac Graft" Apr. 1955 (pp. 510-518).

U.S. Office Action dated Aug. 30, 2010 issued in U.S. Appl. No. 11/748,138, 9 pages.

U.S. Office Action dated Aug. 31, 2010 issued in U.S. Appl. No. 11/748,121, 11 pages.

International Search Report and Written Opinion dated Sep. 21, 2010 issued in PCT Patent Application No. PCT/US2010/043360, 9 pages.

Matthews, Anatomy of the Heart, Definitions Cardiology Explained and Presented by Robert Matthews, MD, http://www.rjmatthewsmd.com/Definitions/anatomy_ofthe_heart.htm, printed Jul. 28, 2008, 265 pages.

Mullens, Vascular access, Cardiac Catheterization in Congenital Heart Disease; Pediatric and Adult, 2006, Chapter 4, pp. 115-117, 5 pages, Blackwell Futura, USA.

Mullens, Aortic valve dilation, Cardiac Catheterization in Congenital Heart Disease; Pediatric and Adult, 2006, Chapter 19, pp. 487-489, 5 pages, Blackwell Futura, USA.

Mullens, Foreign body removal, Cardiac Catheterization in Congenital Heart Disease; Pediatric and Adult, 2006, Chapter 12, pp. 350-377, 30 pages, Blackwell Futura, USA.

Mullens, Flow directed catheters ("floating" balloon catheters), Cardiac Catheterization in Congenital Heart Disease; Pediatric and Adult, 2006, Chapter 7, pp. 213-221, 9 pages, Blackwell Futura, USA.

Acar et al., Areva: Multicenter Randomized Comparison of Low-Dose Versus Standard-Dose Anticoagulation in Patients With Mechanical Prosthetic Heart Valves, Circulation, Nov. 1, 1996, 2107-12, vol. 94, No. 9.

Acker et al., Mitral valve surgery in heart failure: Insights from the Acorn Clinical Trial, Surgery for Acquired Cardiovascular Disease, The Journal of Thoracic and Cardiovascular Surgery, Sep. 2006, 568-577.e4, vol. 132, No. 3.

Babaliaros et al., Emerging Applications for Transseptal Left Heart Catheterization—Old Techniques for New Procedures, Journal of the American College of Cardiology, Jun. 3, 2008, 2116-22, vol. 51, No. 22.

Kuck et al., Best of Structural Heart Disease Abstracts, TCT-124, The American Journal of Cardiology, Oct. 20-25, 2007, 58L.

Rinaldi et al., Best of Structural Heart Disease Abstracts, TCT-123, The American Journal of Cardiology, Oct. 20-25, 2007, 57L.

Siminiak et al., Best of Structural Heart Disease Abstracts, TCT-125, The American Journal of Cardiology, Oct. 20-25, 2007, 58L.

B-Lundqvist et al., Transseptal Left Heart Catheterization: A Review of 278 Studies, Clin. Cardiol., Jan. 1986, 21-26, vol. 9.

Bonow et al., ACC/AHA 2006 Guidelines for the Management of Patients With Valvular Heart Disease: Executive Summary, Circulation—Journal of the American Heart Association, Downloaded from circ.ahajournals.org, Jul. 31, 2008, 449-527.

Braunberger et al., Very Long-Term Results (More Than 20 Years) of Valve Repair With Carpentier's Techniques in Nonrheumatic Mitral Valve Insufficiency, Downloaded from circ.ahajournals.org, Aug. 26, 2008, I-8-I-11.

Bryan et al., Prospective randomized comparison of CarboMedics and St. Jude Medical bileaflet mechanical heart valve prostheses: Ten-year follow-up, The Journal of Thoracic and Cardiovascular Surgery, Mar. 2007, 614-622.e2, vol. 133, No. 3.

Burkhoff et al., A randomized multicenter clinical study to evaluate the safety and efficacy of the TandemHeart percutaneous ventricular assist device versus conventional therapy with intraaortic balloon pumping for treatment of cardiogenic shock, American Heart Journal, Sep. 2006, 469.e1-469.e8, vol. 152, No. 3.

Byrne et al, Percutaneous Mitral Annular Reduction Provides Continued Benefit in an Ovine Model of Dilated Cardiomyopathy, Downloaded from circ.ahajournals.org, Aug. 26, 2008, 3088-92.

Carpentier et al., Reconstructive surgery of mitral valve incompetence Ten-year appraisal, The Journal of Thoracic and Cardiovascular Surgery, Mar. 1980, 338-348, vol. 79, No. 3.

Casselman et al., Mitral Valve Surgery Can Now Routinely Be Performed Endoscopically, Downloaded from circ. ahajournals.org, Aug. 26, 2008, II-48-II-54.

Cauchemez et al., High-Flow Perfusion of Sheaths for Prevention of Thromboembolic Complications During Complex Catheter Ablation in the Left Atrium, Journal of Cardiovascular Electrophysiology, Mar. 2004, 276-283, vol. 15, No. 3.

ClinicalTrials.gov, Aachen Safety and Efficacy of the Percutaneous Transvenous Mitral Annuloplasty Device to Reduce Mitral Regurgitation (PTOLEMY), http://clinicaltrials.gov/ct2/show/NCT00572091?term=mitral+regurgitation&rank=2, Aug. 25, 2008, 1-3.

ClinicalTrials.gov, Feasibility Study of a Percutaneous Mitral Valve Repair System., http://clinicaltrials.gov/ct2/show/NCT00209339?term=mitral+valve&rank=3, Aug. 25, 2008, 1-4.

ClinicalTrials.gov, Montreal Safety and Efficacy of the Percutaneous Transvenous Mitral Annuloplasty Device (PTOLEMY), http://clinicaltrials.gov/ct2/show/NCT00571610?term=mitral+regurgitation&rank=13, Aug. 25, 2008, 1-4.

ClinicalTrials.gov, Pivotal Study of a Percutaneous Mitral Valve Repair System, http://clinicaltrials.gov/ct2/show/NCT00209274?term=mitral+valve&rank=1, Aug. 25, 2008, 1-4.

ClinicalTrials.gov, RESTOR-MV: Randomized Evaluation of a Surgical Treatment for Off-Pump Repair of the Mitral Valve, http://clinicaltrials.gov/ct2/show/NCT00120276?term=myocor&rank=1, Aug. 25, 2008, 1-5.

ClinicalTrials.gov, Safety and Efficacy of the Percutaneous Transvenous Mitral Annuloplasty Device to Reduce Mitral Regurgitation (PTOLEMY), http://clinicaltrials.gov/ct2/show/NCT00568230?term=mitral+valve&rank=53, Aug. 25, 2008, 1-3.

ClinicalTrials.gov, VIVID-Valvular and Ventricular Improvement Via iCoapsys Delivery—Feasibility Study, http://clinicaltrials.gov/ct2/show/NCT00512005?term=mitral+valve&rank=12, Aug. 25, 2008, 1-4.

Crabtree et al., Recurrent Mitral Regurgitation and Risk Factors for Early and Late Mortality After Mitral Valve Repair for Functional Ischemic Mitral Regurgitation, The Society of Thoracic Surgeons, 2008, 1537-43, 85.

Criber et al., Early Experience With Percutaneous Transcatheter Implantation of Heart Valve Prosthesis for the Treatment of End-Stage Inoperable Patients With Calcific Aortic Stenosis, Journal of the American College of Cardiology, Feb. 18, 2004, 698-703, vol. 43, No. 4.

De Bonis et al., Similar long-term results of mitral valve repair for anterior compared with posterior leaflet prolapse, The Journal of Thoracic and Cardiovascular Surgery, Feb. 2006, 364-370, vol. 131, No. 2.

Deloche et al., Valve repair with Carpentier techniques The second decade, The Journal of Thoracic and Cardiovascular Surgery, Jun. 1990, 990-1002, vol. 99, No. 6.

De Simone et al., A clinical study of annular geometry and dynamics in patients with ischemic mitral regurgitation: new insights into asymmetrical ring annuloplasty, European Journal of Cardio-thoracic Surgery, 2006, 355-361, 29.

Detaint et al., Surgical Correction of Mitral Regurgitation in the Elderly—Outcomes and Recent Improvements, Downloaded from circ.ahajournals.org, Aug. 26, 2008, 265-272.

Dubreuil et al., Percutaneous Mitral Valve Annuloplasty for Ischemic Mitral Regurgitation: First in Man Experience With a Tempory Implant, Catheterization and Cardiovascular Interventions, 2007, 1053-61, 69.

Duffy et al., Feasibility and Short-Term Efficacy of Percutaneous Mitral Annular Reduction for the Therapy of Funcitonal Mitral Regurgitation in Patients With Heart Failure, Catheterization and Cardiovascular Interventions, 2006, 205-210, 68.

Epstein et al., Gross and Microscopic Pathological Changes Associated With Nonthoracotomy Implantable Defibrillator Leads, Downloaded from circ.ahajournals.org, Jul. 23, 2008, 1517-24.

Epstein et al., Embolic Complications Associated With Radiofrequency Catheter Ablation, The American Journal of Cardiology, Mar. 15, 1996, 655-658, vol. 77.

(56) References Cited

OTHER PUBLICATIONS

Fagundes et al., Safety of Single Transseptal Puncture for Ablation of Atrial Fibrillation: Retrospective Study from a Large Cohort of Patients, Journal of Cardiovascular Electrophysiology, Dec. 2007, 1277-81, vol. 18, No. 12.

Feldman et al., Patient selection for percutaneous mitral valve repair: insight from early clinical trial applications, Nature Clinical Practice Cardiovascular Medicine, Feb. 2008, 84-90, vol. 5, No. 2.

Feldman et al., Percutaneous Mitral Valve Repair Using the Edge-to-Edge Technique—Six-Month Results of the Everest Phase I Clinical Trial, Journal of the American College of Cardiology, Dec. 6, 2005, 2134-40, vol. 46, No. 11.

Fernandez et al., Early and late-phase events after valve replacement with the St. Jude Medical prosthesis in 1200 patients, The Journal of Thoracic and Cardiovascular Surgery, Feb. 1994, 394-407, vol. 107, No. 2.

Gillinov et al., Durability of Mitral Valve Repair for Degenerative Disease, The Journal of Thoracic and Cardiovascular Surgery, Nov. 1998, 734-743, vol. 116, No. 5.

Grossi et al., Intraoperative Effects of the Coapsys Annuloplasty System in a Randomized Evaluation (RESTOR-MV) of Functional Ischemic Mitral Regurgitation, The Society of Thoracic Surgeons, 2005, 1706-11, 80.

Grossi et al., Late Results of Mitral Valve Reconstruction in the Elderly, The Society of Thoracic Surgeons, 2000, 1224-6, 70.

Grossi et al., Minimally Invasive Mitral Valve Surgery: A 6-Year Experience With 714 Patients, The Society of Thoracic Surgeons, 2002, 660-4, 74.

Hendren et al., Mitral Valve Repair for Ischemic Mitral Insufficiency, The Society of Thoracic Surgeons, 1991, 1246-52, 52.

Heupler et al., Infection Prevention Guidelines for Cardiac Catheterization Laboratories, Catheterization and Cardiovascular Diagnosis, 1992, 260-263, 25.

Hvass et al., Papillary Muscle Sling: A New Functional Approach to Mitral Repair in Patients With Ischemic Left Ventricular Dysfunction and Functional Mitral Regurgitation, The Society of Thoracic Surgeons, 2003, 809-11, 75.

Ibrahim et al., The St. Jude Medical prosthesis—A thirteen-year experience, The Journal of Thoracic and Cardiovascular Surgery, Aug. 1994, 221-230, vol. 108, No. 2.

Iskandar et al., Tricuspid Valve Malfunction and Ventricular Pacemaker Lead: Case Report and Review of the Literature, Echocardiography: A Jrnl of CV Ultrasound & Allied Tech., 2006, 692-697, vol. 23, No. 8.

Kasegawa et al., Mitral Valve Repair for Anterior Leaflet Prolapse With Expanded Polytetrafluoroethylene Sutures, The Society of Thoracic Surgeons, 2006, 1625-31, 81.

Kaye et al., Feasibility and Short-Term Efficacy of Percutaneous Mitral Annular Reduction for the Therapy of Heart Failure-Induced Mitral Regurgitation, Downloaded from circ.ahajournals.org, Aug. 26, 2008, 1795-97.

International Search Report and Written Opinion dated Sep. 22, 2008 issued in PCT Application No. PCT/US08/63560, 11 pages.

International Search Report and Written Opinion dated Sep. 29, 2008 issued in PCT Application No. PCT/US08/63568, 12 pages.

Canadian Office Action dated Sep. 18, 2012 issued in Canadian Patent Application No. 2,627,517, 2 pages.

Intent to Grant dated Jan. 2, 2013 issued in European Patent Application No. 06816336.9, 7 pages.

Notice of Allowance dated Jan. 9, 2013 issued in U.S. Appl. No. 11/748,121, 7 pages.

U.S. Office Action dated Oct. 9, 2012, issued in U.S. Appl. No. 12,872,228, 7 pages.

U.S. Notice of Allowance dated Nov. 21, 2012, issued in U.S. Appl. No. 11/748,121, 8 pages.

European Intent to Grant dated Feb. 22, 2013 issued in European Patent Application No. 08 755 418.4, 7 pages.

European Search Report dated Mar. 6, 2013 issued in European Patent Application No. 10804952.9, 8 pages.

Notice of Allowance dated Mar. 8, 2013 issued in U.S. Appl. No. 11/748,138, 9 pages.

Final Office Action dated Mar. 13, 2013 issued in U.S. Appl. No. 11/748,147, 10 pages.

Notice of Allowance dated Apr. 11, 2013 issued in U.S. Appl. No. 13/545,927, 12 pages.

Supplemental Notice of Allowability dated May 2, 2013 issued in U.S. Appl. No. 13/545,927, 5 pages.

Notice of Allowance dated Jul. 8, 2013 issued in Canadian Patent Application No. 2,627,517, 1 page.

Notice of Allowance dated Jun. 3, 2013 issued in U.S. Appl. No. 12/872,228, 7 pages.

Final Office Action dated Jun. 19, 2013 issued in U.S. Appl. No. 11/748,147, 10 pages.

Notice of Allowance dated Aug. 12, 2013 issued in U.S. Appl. No. 11/940,724, 26 pages.

* cited by examiner

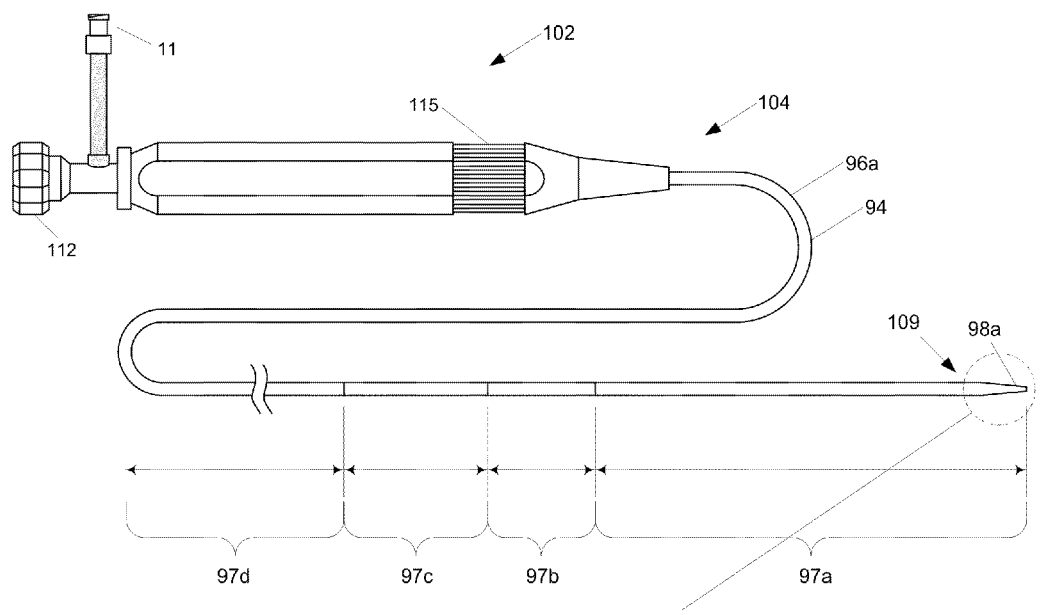

FIGURE 14A
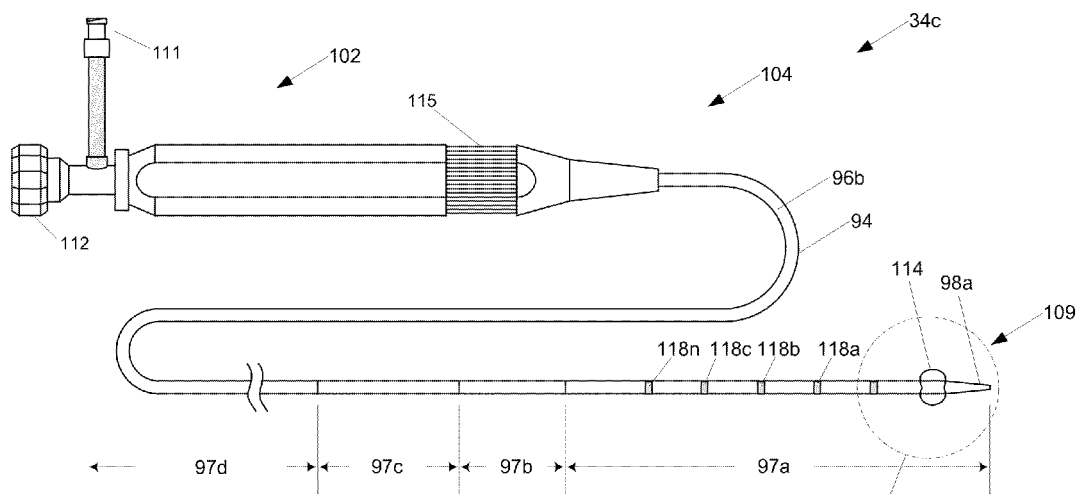
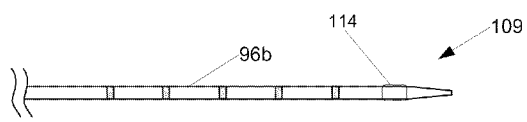
FIGURE 14B
Close-up section of tip
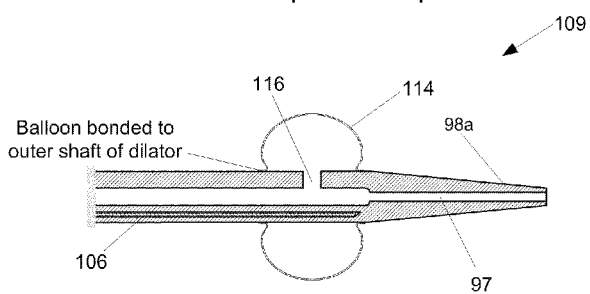
FIGURE 14C
Balloon bonded to outer shaft of dilator

FIGURE 20A
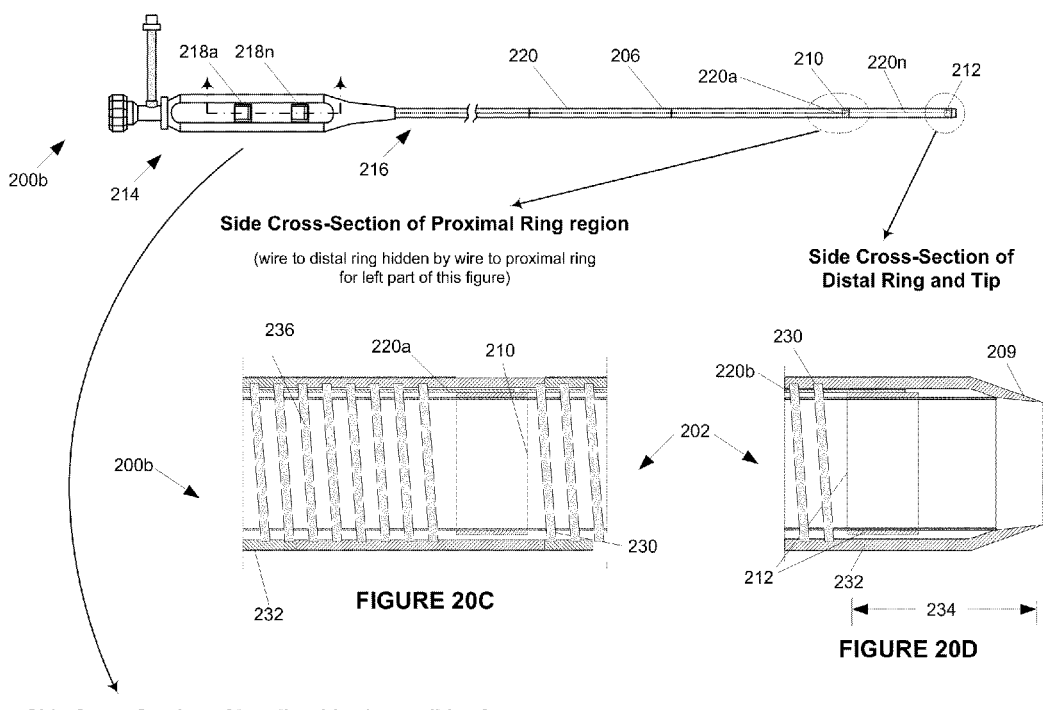
FIGURE 20C
FIGURE 20D
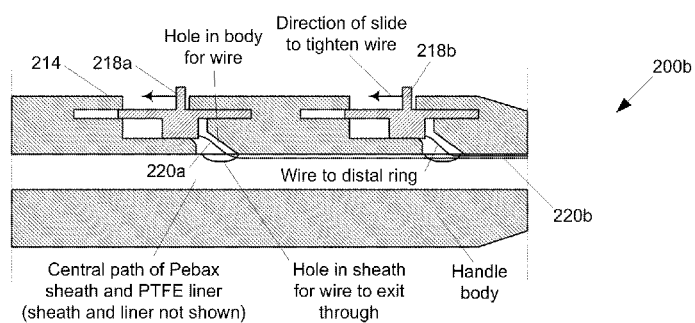
FIGURE 20B

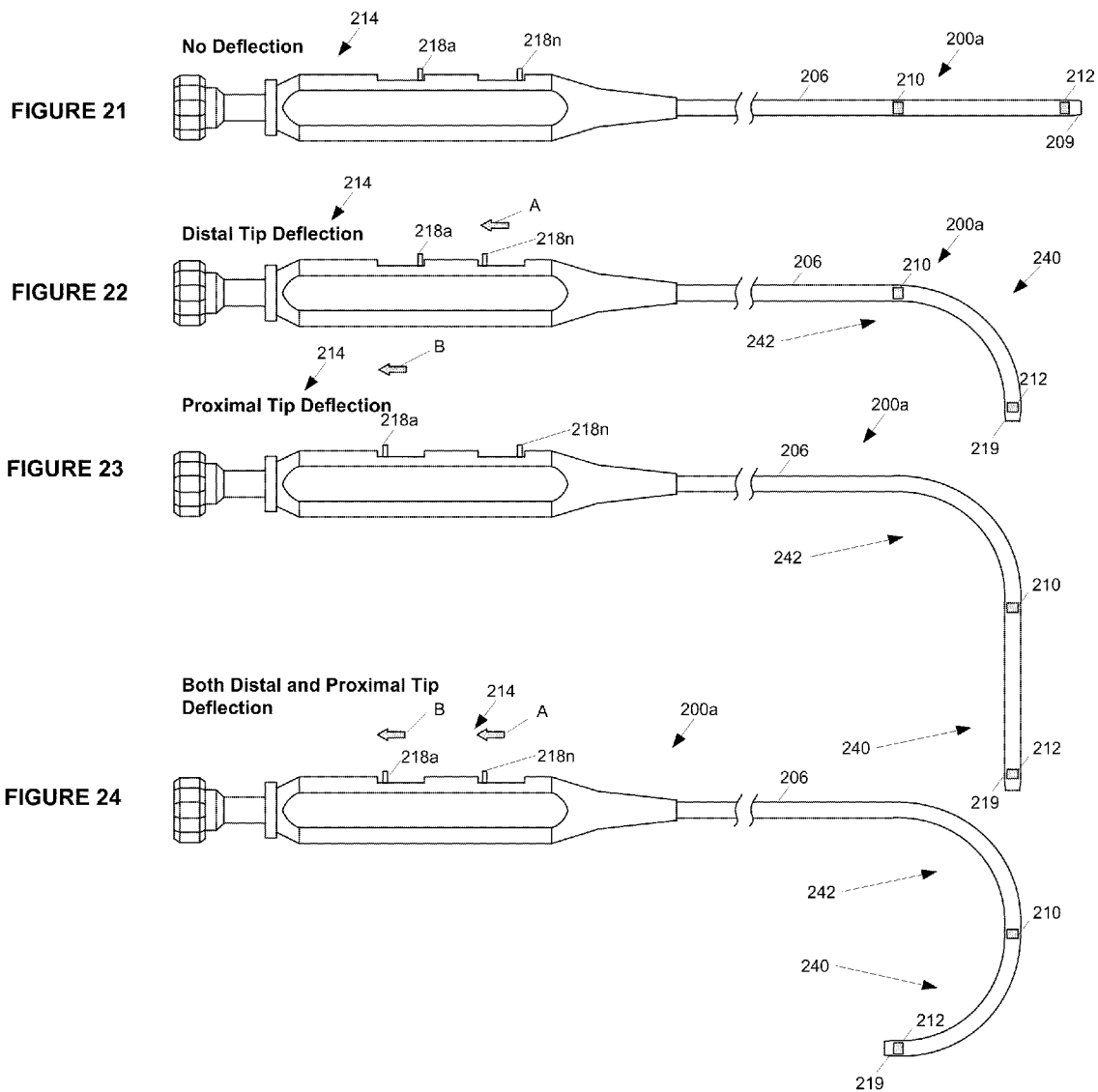

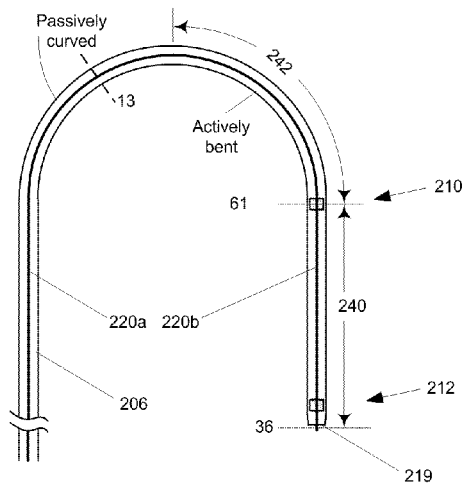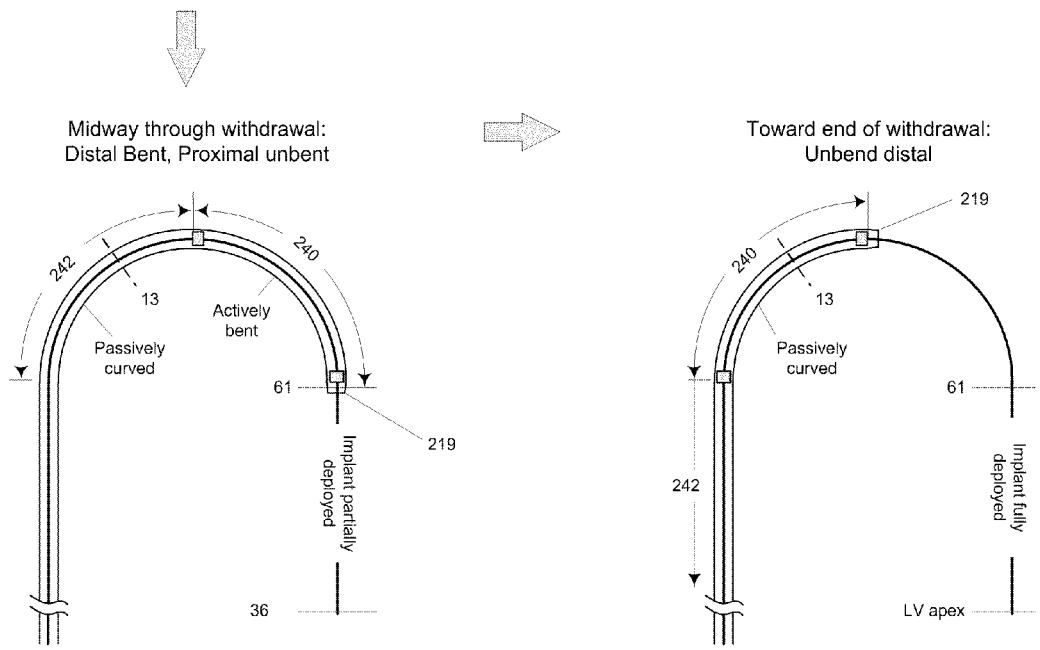

STEERABLE CATHETER AND DILATOR AND SYSTEM AND METHOD FOR IMPLANTING A HEART IMPLANT

CROSS REFERENCE TO RELATED APPLICATIONS

The present application is a continuation-in-part of U.S. patent application Ser. No. 12/209,686 filed Sep. 12, 2008, which claims the benefit of U.S. Provisional Application Ser. No. 61/061,343, filed Jun. 13, 2008, both of which are hereby incorporated fully by reference.

FIELD

The present disclosure relates to the repair and/or correction of dysfunctional heart valves, and more particularly pertains to heart valve implants and systems and methods for delivery and implementation of the same.

BACKGROUND

A human heart has four chambers, the left and right atrium and the left and right ventricles. The chambers of the heart alternately expand and contract to pump blood through the vessels of the body. The cycle of the heart includes the simultaneous contraction of the left and right atria, passing blood from the atria to the left and right ventricles. The left and right ventricles then simultaneously contract forcing blood from the heart and through the vessels of the body. In addition to the four chambers, the heart also includes a check valve at the upstream end of each chamber to ensure that blood flows in the correct direction through the body as the heart chambers expand and contract. These valves may become damaged, or otherwise fail to function properly, resulting in their inability to properly close when the downstream chamber contracts. Failure of the valves to properly close may allow blood to flow backward through the valve resulting in decreased blood flow and lower blood pressure.

Mitral regurgitation is a common variety of heart valve dysfunction or insufficiency. Mitral regurgitation occurs when the mitral valve separating the left coronary atrium and the left ventricle fails to properly close. As a result, upon contraction of the left ventricle blood may leak or flow from the left ventricle back into the left atrium, rather than being forced through the aorta. Any disorder that weakens or damages the mitral valve can prevent it from closing properly, thereby causing leakage or regurgitation. Mitral regurgitation is considered to be chronic when the condition persists rather than occurring for only a short period of time.

Regardless of the cause, mitral regurgitation may result in a decrease in blood flow through the body (cardiac output). Correction of mitral regurgitation typically requires surgical intervention. Surgical valve repair or replacement may be carried out as an open heart procedure. The repair or replacement surgery may last in the range of about three to five hours, and may be carried out with the patient under general anesthesia. The nature of the surgical procedure requires the patient to be placed on a heart-lung machine. Because of the severity/complexity/danger associated with open heart surgical procedures, corrective surgery for mitral regurgitation is typically not recommended until the patient's ejection fraction drops below 60% and/or the left ventricle is larger than 45 mm at rest.

BRIEF DESCRIPTION OF THE DRAWINGS

Features and advantage of the claimed subject matter will be apparent from the following description of embodiments consistent therewith, which description should be considered in conjunction with the accompanying drawings, wherein:

FIG. 13A illustrates a perspective view of an embodiment of a dilator consistent with the present disclosure;

FIG. 13B illustrates a close-up of one embodiment of the tip of the dilator shown in FIG. 13A consistent with the present disclosure;

FIG. 14A illustrates a perspective view of a yet another embodiment of a dilator consistent with the present disclosure;

FIG. 14B illustrates a perspective view of one embodiment of the dilator shown in a deflected or retracted position consistent with the present disclosure;

FIG. 14C illustrates a perspective view of one embodiment of the dilator shown in an inflated or expanded position consistent with the present disclosure;

FIGS. 20A-D illustrate various views of another embodiment of a steerable catheter consistent with the present disclosure;

FIG. 21 illustrates a perspective view of an embodiment of a steerable catheter in a non-deflected position consistent with the present disclosure;

FIG. 22 illustrates a perspective view of an embodiment of a steerable catheter with the distal tip in a deflected position consistent with the present disclosure;

FIG. 23 illustrates a perspective view of an embodiment of a steerable catheter with the proximal tip in a deflected position consistent with the present disclosure;

FIG. 24 illustrates a perspective view of an embodiment of a steerable catheter with the distal tip and the proximal tip in a deflected position consistent with the present disclosure;

FIGS. 28-30 illustrate one embodiment of a withdrawal sequence for a steerable catheter consistent with the present disclosure.

DESCRIPTION

Figure 1:
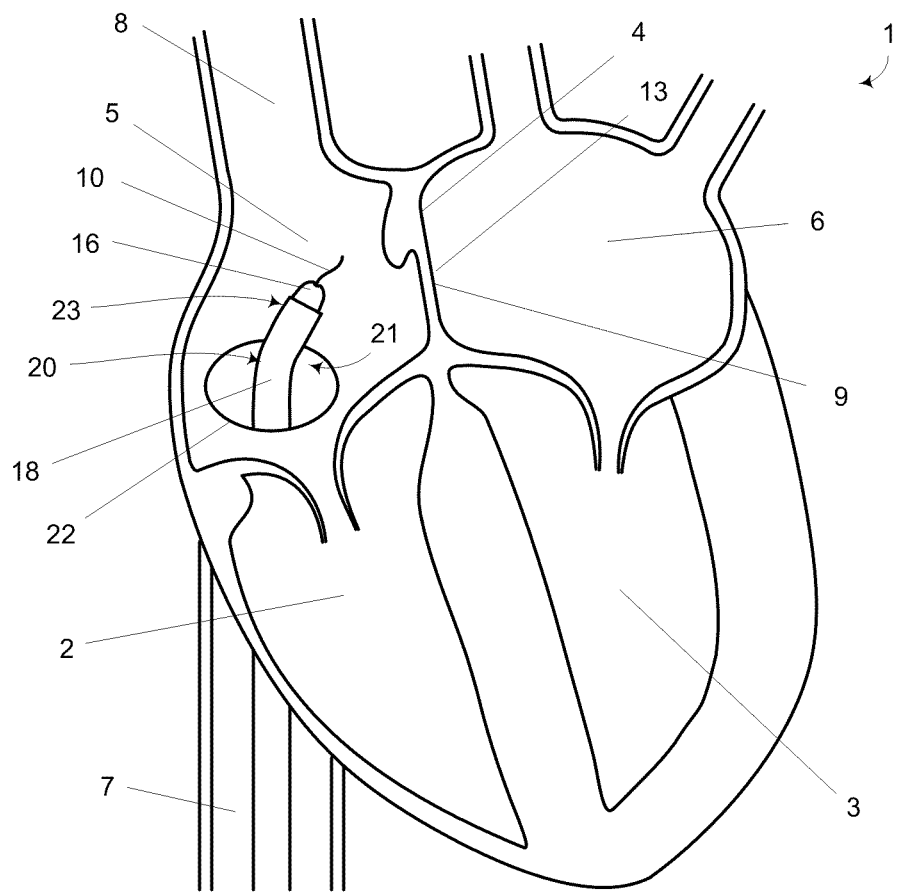
FIG. 1 illustrates a perspective view of an embodiment of a transseptal catheter in the right atrium consistent with the present disclosure.

The present disclosure relates to a system and method of implanting a heart implant. For example, the system and method according to one embodiment of the present disclosure may be used to implant a heart valve implant which may suitably be used in connection with the treatment, diagnostics and/or correction of a dysfunctional or inoperative heart valve. One suitable implementation for a heart valve implant consistent with the present disclosure is the treatment of mitral valve regurgitation. For the ease of explanation, the heart valve implant herein is described in terms of a mitral valve implant, such as may be used in treating mitral valve regurgitation as described in U.S. patent application Ser. No. 11/258,828 filed Oct. 26, 2005 and U.S. patent application Ser. No. 12/209,686 filed Sep. 12, 2008, both of which are fully incorporated herein by reference. However, a heart valve implant consistent with the present disclosure may be employed for treating, diagnosing and/or correcting other dysfunctional or inoperative heart valves. The present disclosure should not, therefore, be construed as being limited to use as a mitral valve implant. In addition, the system and method according to the present disclosure may be used to implant heart implants configured to be used in connection with the treatment, diagnostics and/or correction of other heart conditions. For example, and without limitation, the system and method consistent with the present disclosure may be used to implant a regurgitation implant configured to induce a controlled regurgitation in a heart valve (such as, but not limited to, a mitral heart valve), for example, in a manner that is generally consistent with advanced disease of the heart. The regurgitation implant may include a regurgitation implant as described in U.S. patent Ser. No. 11/940,724 filed Nov. 15, 2007 and U.S. patent application Ser. No. 12/209,686 filed Sep. 12, 2008, both of which are fully incorporated herein by reference.

According to one embodiment, a heart implant consistent with the present disclosure may comprise a heart valve implant configured to interact with at least a portion of an existing heart valve to prevent and/or reduce regurgitation. For example, at least a portion of one or more cusps of the heart valve may interact with, engage, and/or seal against at least a portion of the heart valve implant when the heart valve is in a closed condition. The interaction, engagement and/or sealing between at least a portion of at least one cusp and at least a portion of the heart valve implant may reduce and/or eliminate regurgitation in a heart valve, for example, providing insufficient sealing, including only a single cusp, e.g., following removal of a diseased and/or damaged cusp, and/or having a ruptured cordae. A heart valve implant consistent with the present disclosure may be used in connection with various additional and/or alternative defects and/or deficiencies.

For the ease of explanation, one embodiment of the system and method consistent with the present disclosure is described in terms of a system and method for implanting a mitral valve implant, such as may be used in treating mitral valve regurgitation. By way of an overview, the system and method may generally comprise placing a guide wire into the left ventricle and advancing a mitral valve implant through a delivery catheter and into the left ventricle. For example, a guide wire may be initially placed into the left atrium of the heart, for example, by way of transseptal puncture of the heart from the right atrium through the fossa ovalis into the left atrium. A dilator may then be advanced along the guide wire to the left atrium and may be passed through the mitral valve into the left ventricle. The dilator may include a balloon which may be inflated to facilitate passing the dilator through the mitral valve without damaging the mitral valve or becoming entangled in the mitral valve. A steerable catheter may then be advanced along the dilator into the left ventrical. The steerable catheter may be positioned within the left ventrical to the approximate location in which the implant will be secured. The implant may then be advanced through the steerable catheter and secured to the native cardiac tissue.

Referring now to FIG. 1, a cross-sectional schematic view of a portion of a four chamber heart 1 is illustrated. The outflow tracts of the right and left ventricles 2, 3 are not shown in order to better illustrate the septum 4 between the right and left atria 5, 6. As shown, the inferior vena cava (IVC) 7 and superior vena cava (SVC) 8 communicate with the right atrium 5 which is separated from the left atrium 6 by the intra-atrial septum 4. While not a limitation of the present disclosure, it is may be advantageous to make the transseptal puncture 13 through the fossa ovalis 9 since the fossa ovalis 9 is thinnest portion of the intra-atrial septum 4.

According to one embodiment consistent with the present disclosure, a guide wire 10 may be advanced up the IVC 7 and into the right atrium 5. The guide wire 10 may include any guide wire configured to be advanced up the IVC 7 and into the right atrium 5. Consistent with one embodiment, the guide wire 10 may be the same as the delivery guide wire discussed herein; however, the guide wire 10 may also be separate and distinct from the delivery guide wire. Without limitation, access to the right atrium 5 may be accomplished by way of the Seldinger wire technique. For example, the right femoral vein (not shown) may be accessed with a hollow needle (not shown) and a guide wire 10 may be inserted. The needle may be removed and a dilator 16 may be inserted over the guide wire 10. The sheath 18 of a catheter 20 (such as, but not limited to, a Mullins catheter or the like) having a pre-bent region 21 proximate the distal tip 23 of the catheter 20 may be inserted over the dilator 16. The sheath 18, dilator 16, catheter 20 and guide wire 10 may then be advanced up the IVC 7 through the opening 22 into the right atrium 5 as generally illustrated in FIG. 1.

Figure 2:
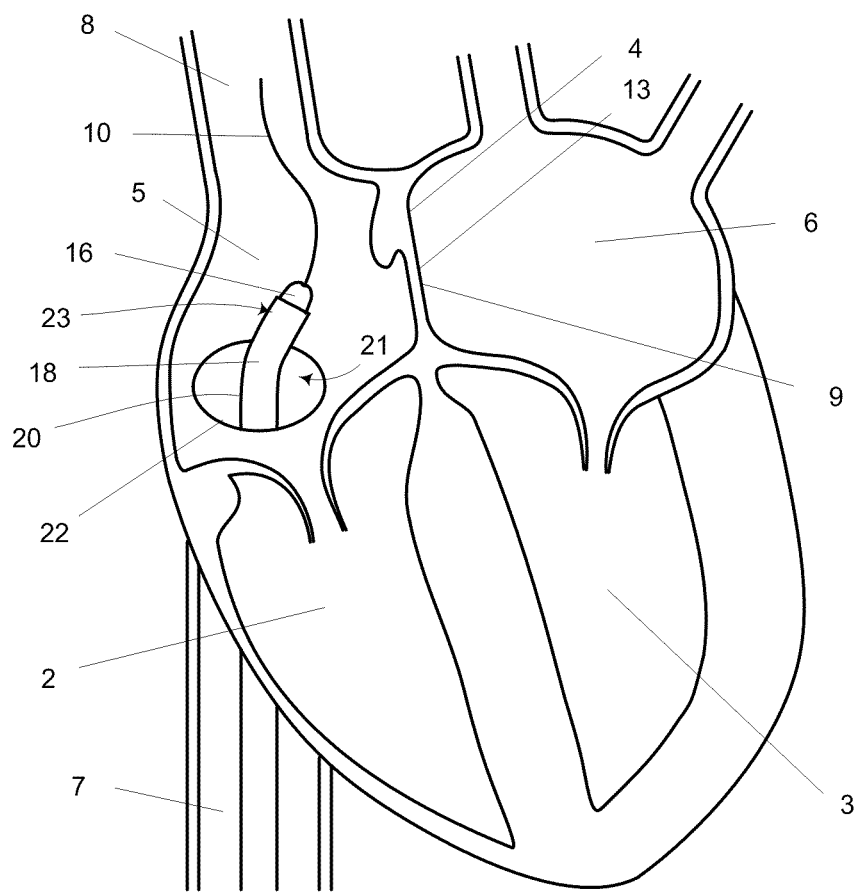
FIG. 2 illustrates a perspective view of an embodiment of a guide wire advanced into the superior vena cava consistent with the present disclosure.
Figure 3:
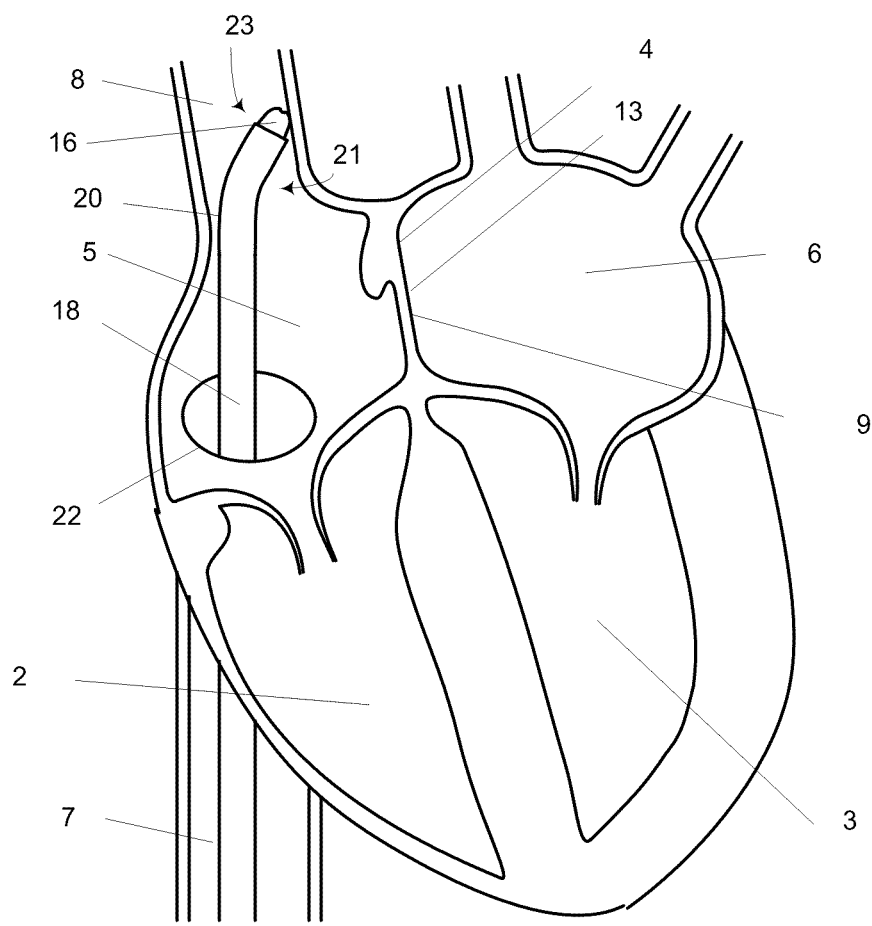
FIG. 3 illustrates a perspective view of an embodiment of a catheter advanced into the superior vena cava consistent with the present disclosure.

With the sheath 18, dilator 16, catheter 20 and guide wire 10 in the right atrium 5, access to the left atrium 6 may be achieved by transseptal puncture 13 from the right atrium 5 through the intra-atrial septum 4. For example, at least a portion of the guide wire 10 may be advanced out of the distal tip 23 of the dilator 16, sheath 18 and/or catheter 20 as generally shown in FIG. 2. According to an embodiment, the guide wire 10 may be at least partially advanced into the SVC 8 as generally illustrated in FIG. 2 and the distal tip 23 of the catheter 20 may then be at least partially advanced along the guide wire 10 into the SVC 8 as generally illustrated in FIG. 3. Because the SVC 8 is a thin-walled vein, it may be advantageous to place the guide wire 10 in the SVC 8 and then advance the catheter 20 along the guide wire 10 since the spring-tipped atraumatic guide wire 10 reduces the potential for damaging the SVC 8 compared to the catheter 20 and dilator 16.

Figure 4:
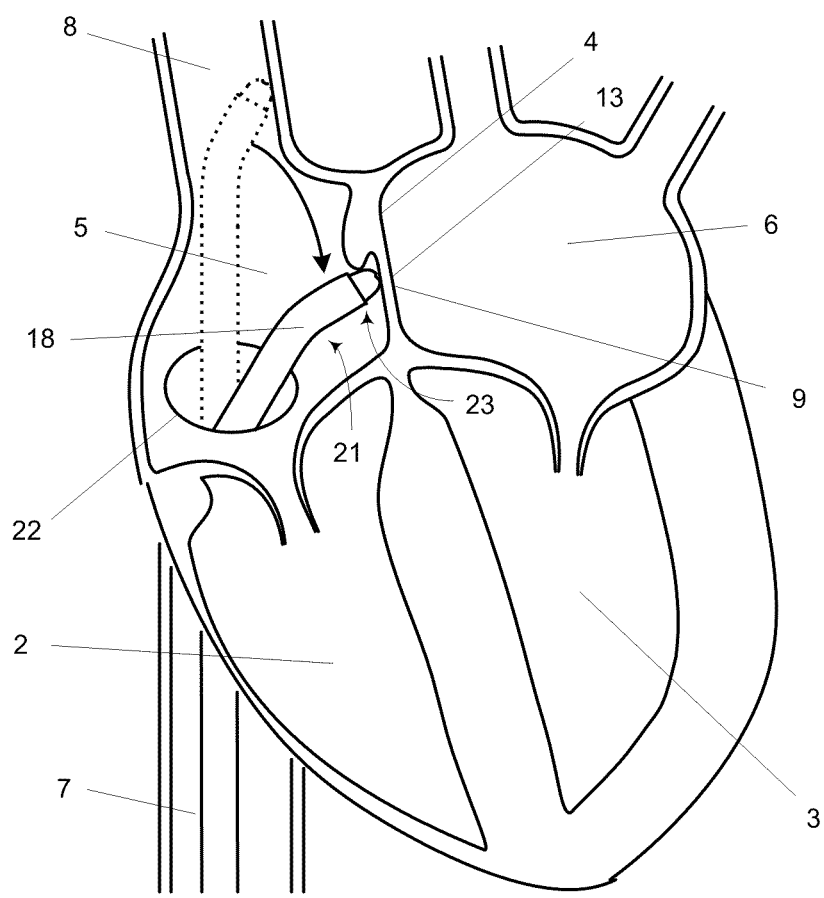
FIG. 4 illustrates a perspective view of an embodiment of a catheter tip against the fossa ovalis consistent with the present disclosure.
Figure 5:
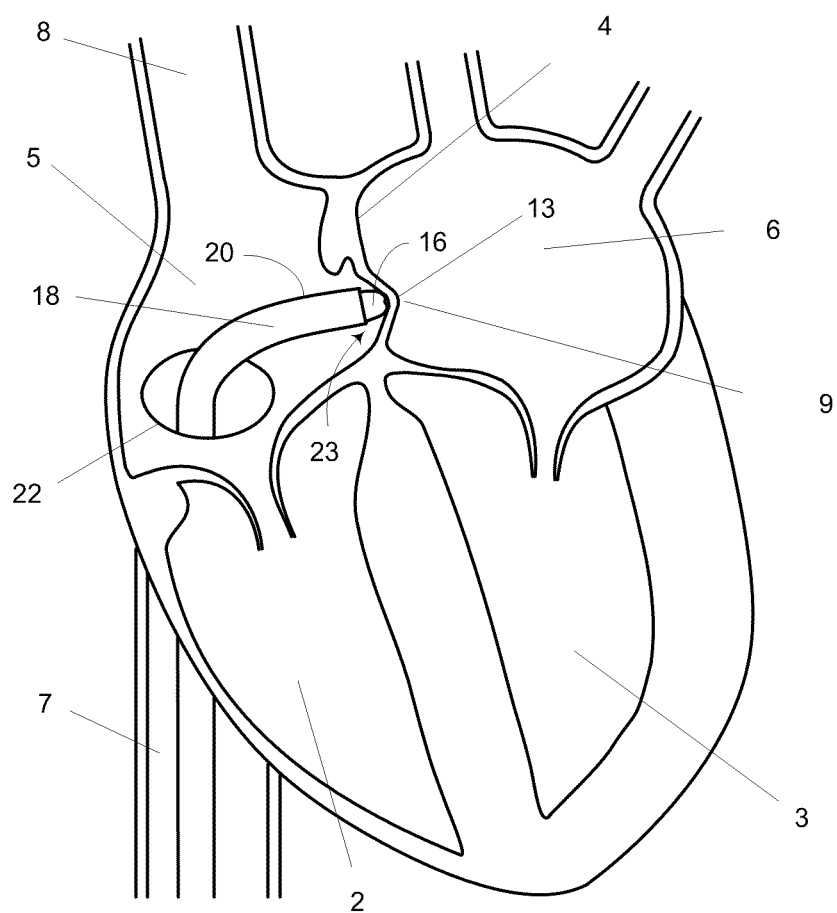
FIG. 5 illustrates a perspective view of an embodiment of a catheter tenting the fossa ovalis consistent with the present disclosure.

With the distal tip 23 at least partially received in the SVC 8, the guide wire 10 may be retracted into the dilator 16 and the catheter 20 may be retracted (i.e., pulled downward) such that the pre-bent portion 21 of the sheath 18 facilitates guiding the distal tip 23 to the fossa ovalis 9 as generally illustrated in FIG. 4. For example, using one or more visualization techniques (such as, but not limited to, intracardiac echo (ICE), fluoroscopy, and the like), the sheath 18 may be retracted proximally, dragging the distal tip 23 along the intra-atrial septum 4 until the distal tip 23 is positioned proximate to the fossa ovalis 9. Optionally, the position of the sheath 18 relative to the fossa ovalis 9 may be confirmed by gently pushing the sheath 18 distally against the intra-atrial septum 4 to "tent" the fossa ovalis 9 as generally illustrated in FIG. 5. The "tenting" of the fossa ovalis 9 may be seen on ICE, fluoroscopy or the like.

Figure 6:
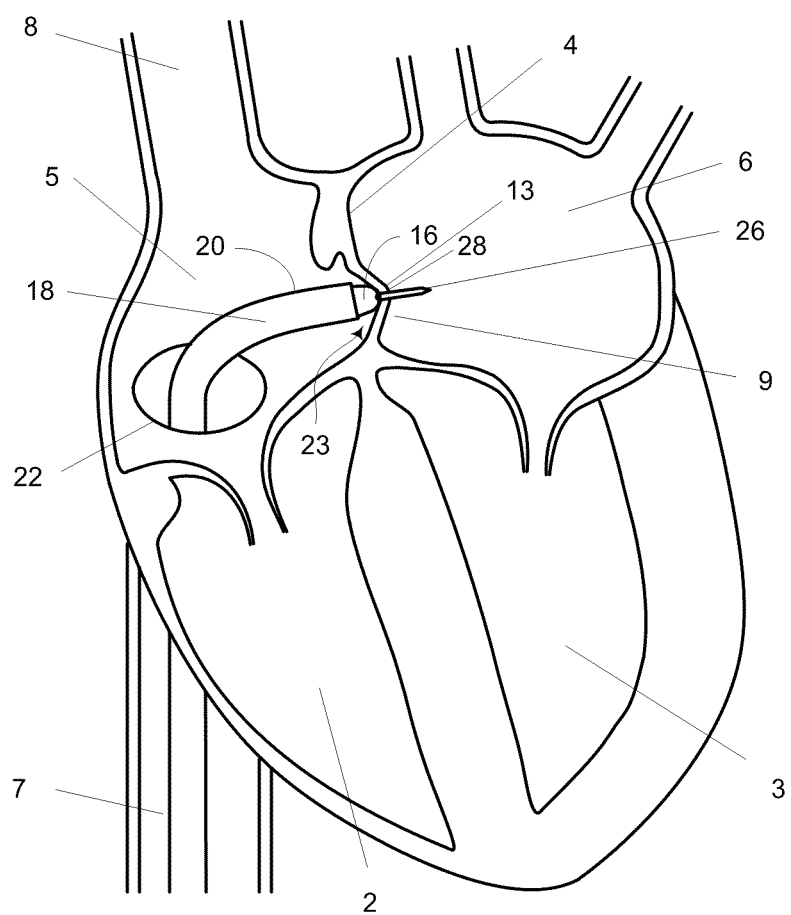
FIG. 6 illustrates a perspective view of an embodiment of a needle puncturing the fossa ovalis consistent with the present disclosure.
Figure 7:
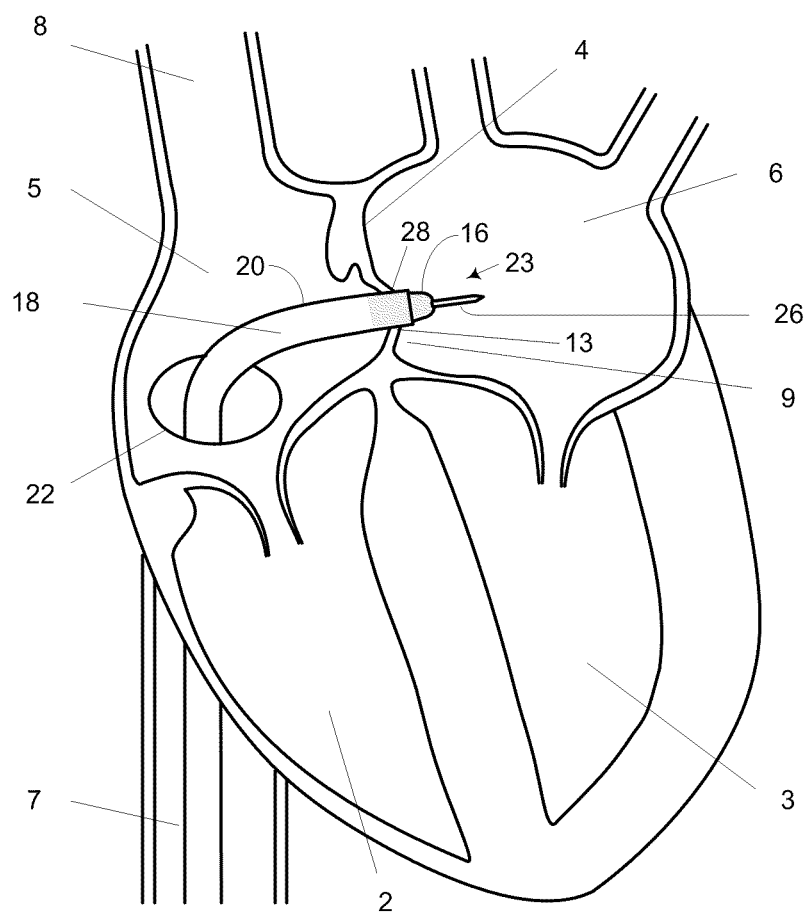
FIG. 7 illustrates a perspective view of an embodiment of a transseptal catheter punctured through the fossa ovalis consistent with the present disclosure.
Figure 8:
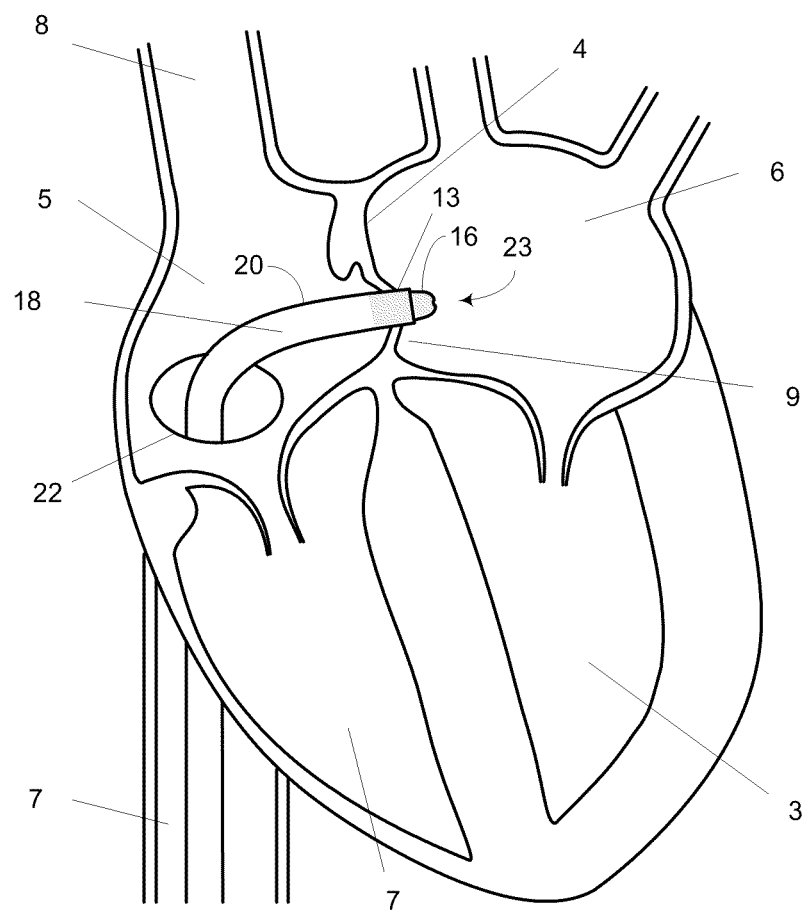
FIG. 8 illustrates a perspective view of an embodiment of a transseptal catheter in the left atrium with the needle removed consistent with the present disclosure.

With the distal tip 23 proximate and/or contacting the fossa ovalis 9, the guide wire 10 may be removed from the catheter 20 and a transseptal needle 26 may be advanced through the catheter 20 towards the distal end 23 of the catheter 20 as generally shown in FIG. 6. The position of the catheter 20 may optionally be confirmed (for example, but not limited to, by "tenting") and the transseptal needle 26 may be advanced out of the distal tip 23 to form a puncture 28 through the fossa ovalis 9 and into the left atrium 6. The sheath 16, dilator 28 and catheter 20 may than be advanced through the puncture 28 of the fossa ovalis 9 and into the left atrium 6 as generally shown in FIG. 7. Once the sheath 16, dilator 28 and catheter 20 are through the fossa ovalis 9, the needle 26 may be removed from the catheter 20 as generally shown in FIG. 8.

Figure 9:
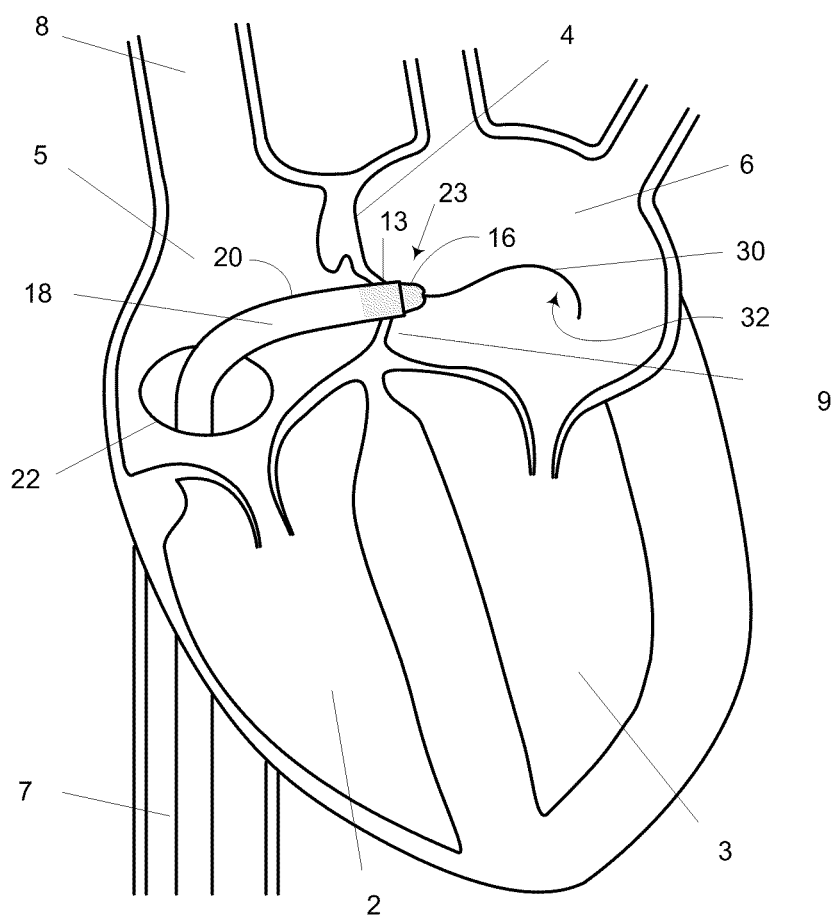
FIG. 9 illustrates a perspective view of an embodiment of a rail advanced into the right atrium through the transseptal catheter consistent with the present disclosure.
Figure 10:
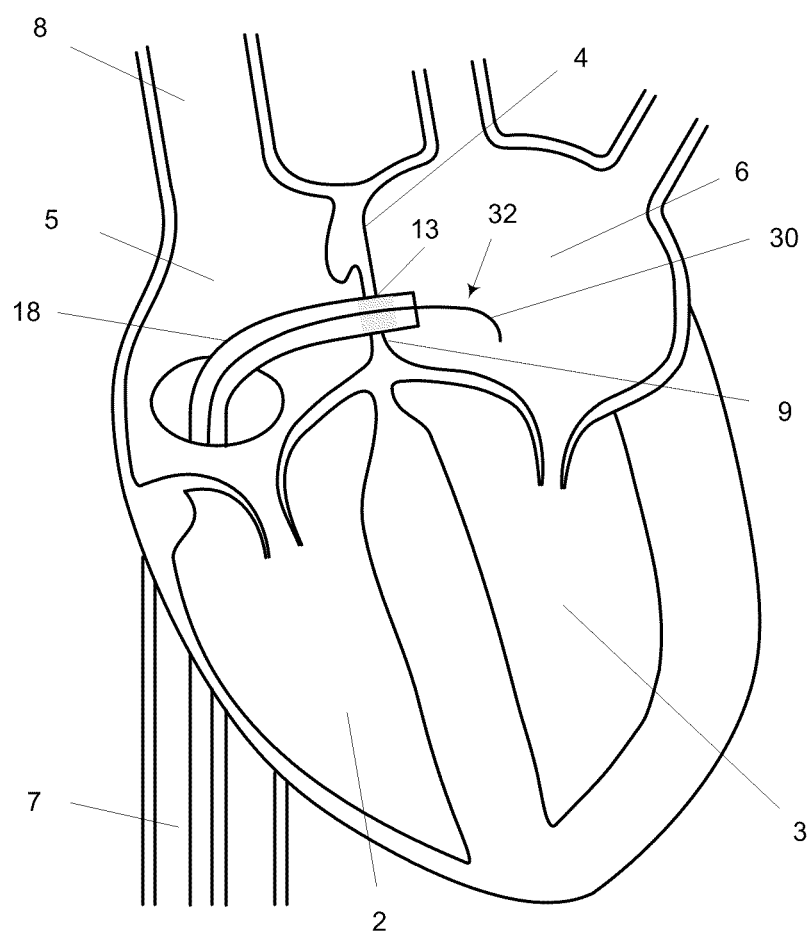
FIG. 10 illustrates a perspective view of an embodiment of a sheath and dilator removed with a rail in the right atrium consistent with the present disclosure.

With the catheter 20 in the left atrium 6, a delivery guide wire 30 may be advanced through the catheter 20 until at least a portion of the distal tip 32 of the delivery guide wire 30 extends from the distal tip 23 of the catheter 20 and into the left atrium 6 as generally illustrated in FIG. 9. Once the distal tip 32 of the delivery guide wire 30 is disposed in the left atrium 6, the dilator 16 and the sheath 18 may be removed, leaving just the delivery guide wire 30 in the left atrium 6 as generally illustrated in FIG. 10.

The delivery guide wire 30 may be used as a guide for advancing other devices into the heart 1, and ultimately, into the left ventricle 3. Accordingly to at least one embodiment, the delivery guide wire 30 may be sufficiently stiff to resist undesirable bending and/or kinking and to resist undesirable movement of the distal tip 32. For example, the delivery guide wire 30 may comprise a stiff, 0.018" diameter guide wire having a stiffness of approximately 19,900,000 psi. The stiffness of the delivery guide wire 30 was determined as follows.

When a force is applied to a long thin column, there is no movement of the column until a minimum critical buckling force is achieved, $P_{cr}$, then further buckling occurs, though the force does not increase. For a long column of uniform cross-section and length 1, which buckles under a critical force, $P_{cr}$, the following formula applies:

$$P_{cr} = n\pi^2 \frac{EI}{L^2}$$

Where:
n=a constant that is equal to 4 if both ends of the column are clamped and cannot move or rotate.
E=Modulus of elasticity of the material (psi)
I=Moment of inertia (in$^4$)
For a circular cross-section the moment of inertia is:

$$I = \frac{\pi d^4}{64}$$

Substituting for I in the first equation for $P_{cr}$ leads to:

$$P_{cr} = n\pi^3 \frac{Ed^4}{64L^2}$$

And solving for the modulus leads to:

$$E = \frac{64L^2 P_{cr}}{n\pi^3 d^4}$$

Based on the above, an 8 cm section of the delivery guide wire 30 was tested and a buckling force of 0.41 lbs. was determined. Therefore, $$E = \frac{64(3.15)^2(0.41)}{4\pi^3(0.018)^4} = 19,900,000 \text{ psi}$$

This stiffness of the delivery guide wire 30 may therefore be approximately 19,900,000 psi. Of course, the delivery guide wire 30 may have a stiffness greater than or less than 19,900,000 psi.

According to at least one other embodiment, the delivery guide wire 30 may include a typical 0.018" guide wire (for example a 0.018" angled standard exchange guide wire made by Merit Medical Systems of South Jordan, Utah, Model H20STDA18260EX which was determined to have a stiffness of approximately 1,360,000 psi based on the same methodology). In either embodiment, the delivery guide wire 30 may have a diameter greater than or less than 0.018".

Figure 11:
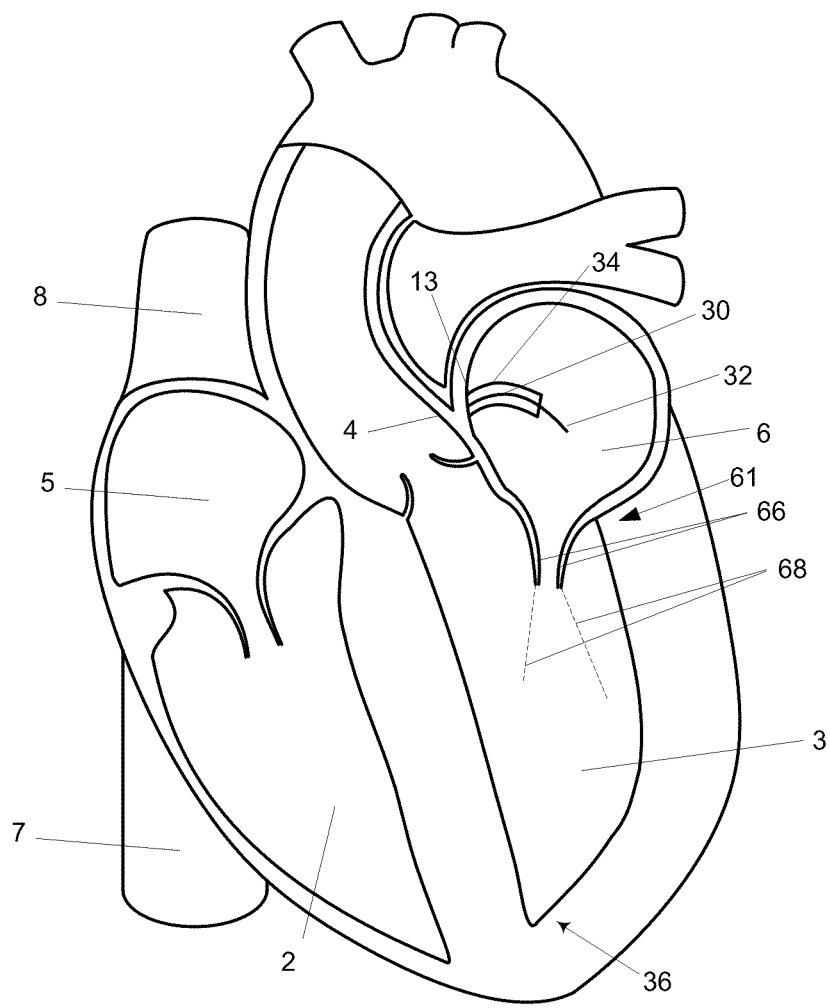
FIG. 11 illustrates a perspective view of an embodiment of a dilator advanced to the left atrium consistent with the present disclosure.

Turning now to FIG. 11, a dilator 34 may be advanced over the delivery guide wire 30 into the left atrium 6. The dilator 34 may be configured to pass through the mitral valve 61 into the left ventricle 3 without damaging the mitral valve 61 or becoming entangled in the mitral valve 61 (for example, the cusps 66, the chordae and/or papillary muscles 68 of the mitral valve 61). According to at least one embodiment, the dilator 34 of the present disclosure may be used to eliminate the rail as disclosed in U.S. patent application Ser. No. 12/209,686 filed Sep. 12, 2008. However, it may be appreciated that the system and method disclosed in the present disclosure (and in particular the dilator 34) is not inconsistent with the system and method in U.S. patent application Ser. No. 12/209,686, and as such, the system and method disclosed in the present disclosure (including the dilator 34) may be used in conjunction with the system and method in U.S. patent application Ser. No. 12/209,686.

Figure 12:
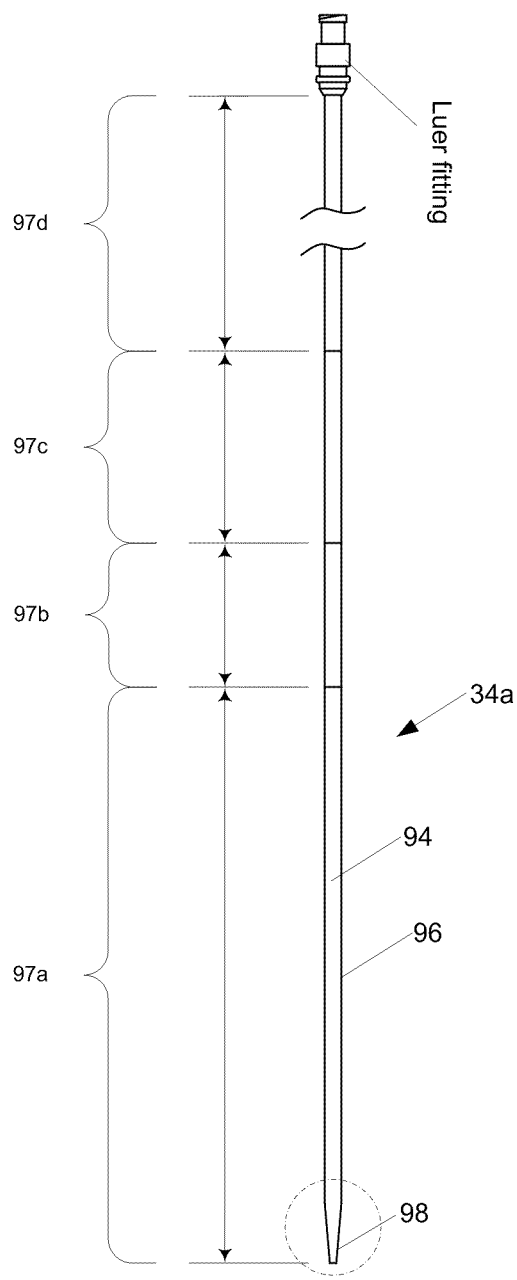
FIG. 12 illustrates a perspective view of one embodiment of a dilator consistent with the present disclosure.

One embodiment of a dilator 34a consistent with the present disclosure is generally illustrated in FIG. 12. The dilator 34a may include define at least one lumen 94 configured to receive at least a portion of the delivery guide wire 30. For example, the lumen 94 may have an internal diameter of approximately 0.038". The dilator 34a may also comprise a shaft 96 including a tapered tip region 98. The shaft 96 may comprise a plurality of segments or portions having different stiffness or hardness to produce the desired overall curvature. The shaft 96 may be formed from one or more suitable polymers such as, but not limited to, a polyether block amide. The shaft 96 may have a constant inner and/or outer diameter and may be made from different materials to provide the various stiffness or hardness. Alternatively, or in addition, the shaft 96 may have different inner and/or outer diameters and may be made from one or more materials. For example, the various stiffness or hardness of the shaft 96 may be provided by varying the thickness of the shaft 96 at the different segments or portions. The different hardness of the segments may provide differing degrees of bending stiffness to the dilator 34a which may facilitate advancing the dilator 34a into and/or out of the left ventricle 3.

As shown, the dilator 34a may comprise four different segments 97a, 97b, 97c and 97d. The first segment 97a may be disposed proximate the distal end region 98. The first segment 97a may optionally include the tapered distal tip 98 and may have a length of approximately 6 inches. The tapered distal tip 98 may be provided to facilitate advancing the tip 98 into the percutaneous puncture site in the groin as the dilator 34a is introduced over the delivery guide wire 30.

According to at least one embodiment, the first segment 97a may be formed of PEBAX™ 3533 having a durometer of 35 D. The second segment 97b may be adjacent to the first segment 97a and may have a length of approximately 1.5 inches. According to at least one embodiment, the second segment 97b may be formed of PEBAX™ 2533 having a durometer of 25 D. The third segment 97c may be adjacent to the second segment 97b and may have a length of approximately 2 inches. According to at least one embodiment, the third segment 97c may be formed of PEBAX™ 3533 having a durometer of 35 D. The forth segment 97d may be adjacent to the third segment 97c and may have a length of approximately 42.5 inches. According to at least one embodiment, the forth segment 97d may be formed of PEBAX™ 7233 having a durometer of 72 D.

It should be understood that the various lengths and hardness described above for the segments 97a-97d may be adjusted or changed depending upon the circumstances of its intended use. For example, patients with larger and/or smaller hearts may require one or more of the segments to be harder or softer. An important aspect of the segments 97a-97d is that the softest segment is the second segment 97b. Also, the second segment 97b is disposed approximately 6 inches from the tapered distal tip 98. As will be explained herein, the location of the second segment 97b may generally correspond to the of the transseptal puncture site 13 where the curvature of the dilator 34a may be greatest.

Turning now to FIGS. 13A and 13B, another embodiment of a dilator 34b consistent with the present disclosure is generally illustrated. The dilator 34 may include a deflectable tip 98a configured to allow the user to bend the distal region 109 of the dilator 34b. The deflectable tip 98a may facilitate advancement of the dilator 34b through the mitral valve 61 may allowing the user to generally aim the tip 98 towards the mitral valve 61. According to at least one embodiment, the dilator 34b may include a handle assembly 102 coupled to a proximal end 104 of the shaft 96a. The shaft 96a may include a plurality of segments, for example, the segments 97a-97d described above. One or more deflecting wires 106 may be coupled to the distal end region 109 of the shaft 96a, for example, as generally illustrated in FIG. 13B. The defecting wire 106 may optionally be disposed in a second lumen 113 disposed along the length of the shaft 96a. Additional defecting wires 106 (not shown) may be provided in one or more additional lumens.

The defecting wire 106 may be coupled to the handle assembly 102 such that the distal tip 98a may be bent as desired. According to one embodiment, the handle assembly 102 may include at least one knob, slider or the like 115 coupled to the defecting wire 106 such that actuation of the knob 115 may result in movement of the distal tip 98a. For example, the knob 115 may be coupled to the defecting wire 106 and may pull the defecting wire 106 generally towards the handle assembly 102 causing the distal tip 98a to bend to one side.

The handle assembly 102 may also optionally include one or more valves or fittings. For example, the handle assembly 102 may include a fitting 111 (such as, but not limited to, a Luer lock fitting or the like) configured to allow the lumen 97 to be flushed. The handle assembly 102 may also optionally include a valve 112 (such as, but not limited to, a hemostasis valve) configured to seal with the delivery guide wire 30 (not shown).

The lumen 97 may have various diameters along the length of the shaft 96a. For example, the lumen 97 may have a smaller diameter proximate the distal tip 98a compared to the remainder of the shaft 96a. The lumen 97 proximate the tip 98a may be slightly larger than the diameter of the delivery guide wire 30 (for example, but not limited to, slightly larger than 0.018") such that the dilator 34a tracks well over the delivery guide wire 30. The remainder of the lumen 97 may have a larger diameter configured to reduce drag as the dilator 34a is advanced over the delivery guide wire 30.

Turning now to FIGS. 14A-14C, yet another embodiment of a dilator 34c consistent with the present disclosure is generally illustrated. The dilator 34c may comprise an expandable device 114 (such as, but not limited to a balloon or the like) configured to facilitate advancement of the dilator 34c through the mitral valve 61 without damaging the mitral valve 61 or becoming entangled in the mitral valve 61 (for example, the cusps 66, the chordae and/or papillary muscles 68 of the mitral valve 61). The expanding portion 114 may be disposed proximate the distal end region 109 of the shaft 96b, for example, substantially adjacent to the tapered tip 98a. The expanding portion 114 may be fluidly coupled to an expanding medium such as, but not limited to, a gas and/or liquid which may expand and/or enlarge the expanding portion 114 from the deflated or retracted position as generally illustrated in FIG. 14B to the inflated or expanded position as generally illustrated in FIG. 14A. According to at least one embodiment, the expanding medium may include carbon dioxide $CO_2$ gas and/or saline. Optionally, contrast media may be introduced into the expanding portion 114 to allow the expanding portion 114 to be more easily visually located using fluoroscopy or the like. The contrast media may coat the inside surface of the expanding portion 114.

The expanding medium may be introduced through a fitting 111. According to at least one embodiment, the expanding medium may be coupled to the expanding portion 114 by way of the lumen 116a as generally illustrated in FIG. 14C. As may be appreciated, the delivery guide wire 30 may be received in the lumen 97 when the dilator 34c is expanded. The expanding medium may be coupled to the expanding portion 114 by way of a separate passageway (i.e., a passageway different from the lumen 97 configured to receive the delivery guide wire 30). This passageway may be the same lumen as the steering wire 106 is housed in, provided there is enough room for the expansion medium to pass around the steering wire.

The expanding portion 114 may include a resiliently expandable/collapsible material such as, but not limited to, silicone, Yulex™ or the like which may be selectively collapsed and/or expanded. The expanding portion 114 may be bonded to the shaft 96b of the dilator 34c and may include one or more passageways, aperture or lumen 116 fluidly coupled to the lumen 97 to allow the expansion medium to expand/collapse the expanding portion 114. The diameter of the expanding portion 114 should be small enough in the first or retracted/collapsed position to be advanced over the delivery guide wire 30 to the left atrium 6 and large enough when in the second or expanded/inflated position to be advanced through the cusps 66 and chordae 68 of the mitral valve 61 to reduce the potential of damaging the heart 1 and/or getting entangled within the mitral valve 61. For example, the shaft 97 may have an outer diameter of approximately 0.062" (e.g., a 5 Fr) and a length of approximately 110 cm or greater. The expanding portion 114 may diameter of approximately 0.100" in the first position and a diameter of approximately 15 mm to approximately 20 mm cm in the second position with a length of approximately 8 to approximately 10 mm.

The dilator 34c may optionally include a deflectable tip 98a configured to allow the user to bend the distal region 109 of the dilator 34b as generally described herein. The dilator 34c may also optionally include one or more radiopaque markers 118a-118n, for example, disposed about the distal end region 109. The position markers 118a-118n may be spaced evenly along the shaft 97 (such as, but not limited to, approximately 2 cm intervals from the distal tip 98a) and may be used to verify the position of the dilator 34c and/or for sizing the implant to be delivered.

While various embodiments of the dilator 34 consistent with the present disclosure have been described herein, it should be understood that one or more features of any of the various embodiments may be combined with any other embodiment. The dilator 34 consistent with the present disclosure may have an overall length (i.e., from the distal tip 98 to the handle assembly 102 of approximately 145 cm or less. However, the length and/or the diameter of the dilator 34 may depend upon the introduction site as well as the intended patient's physiology.

Figure 15:
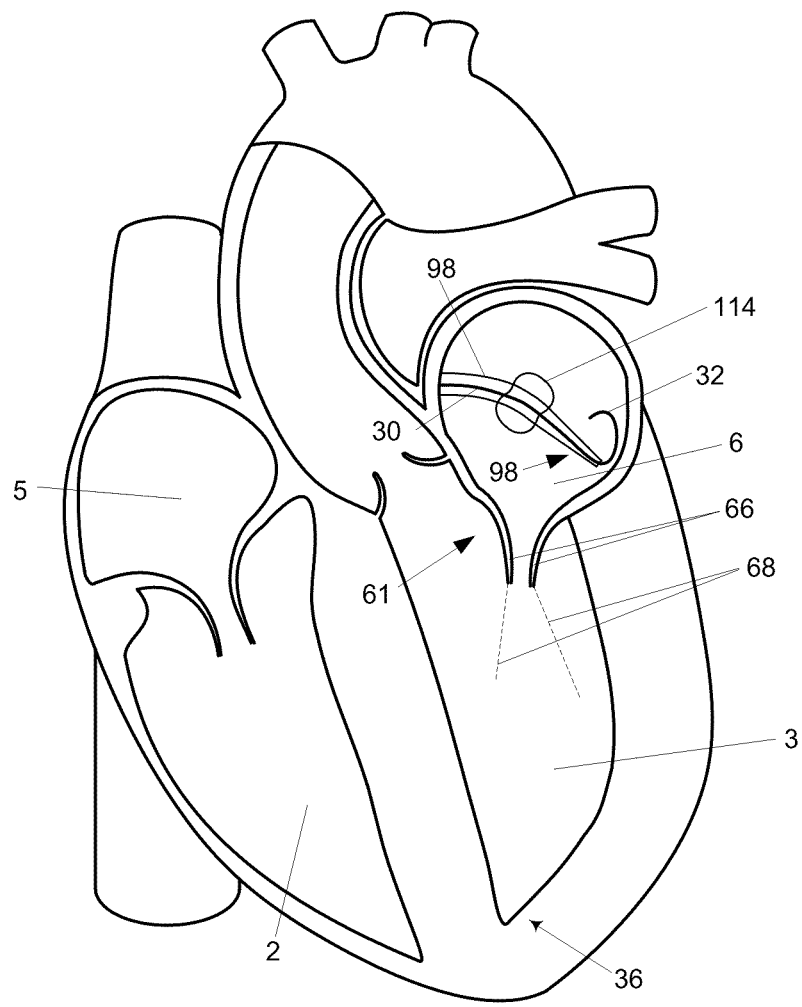
FIG. 15 illustrates a perspective view of a dilator in the inflated or expanded position located in the left atrium consistent with the present disclosure.
Figure 16:
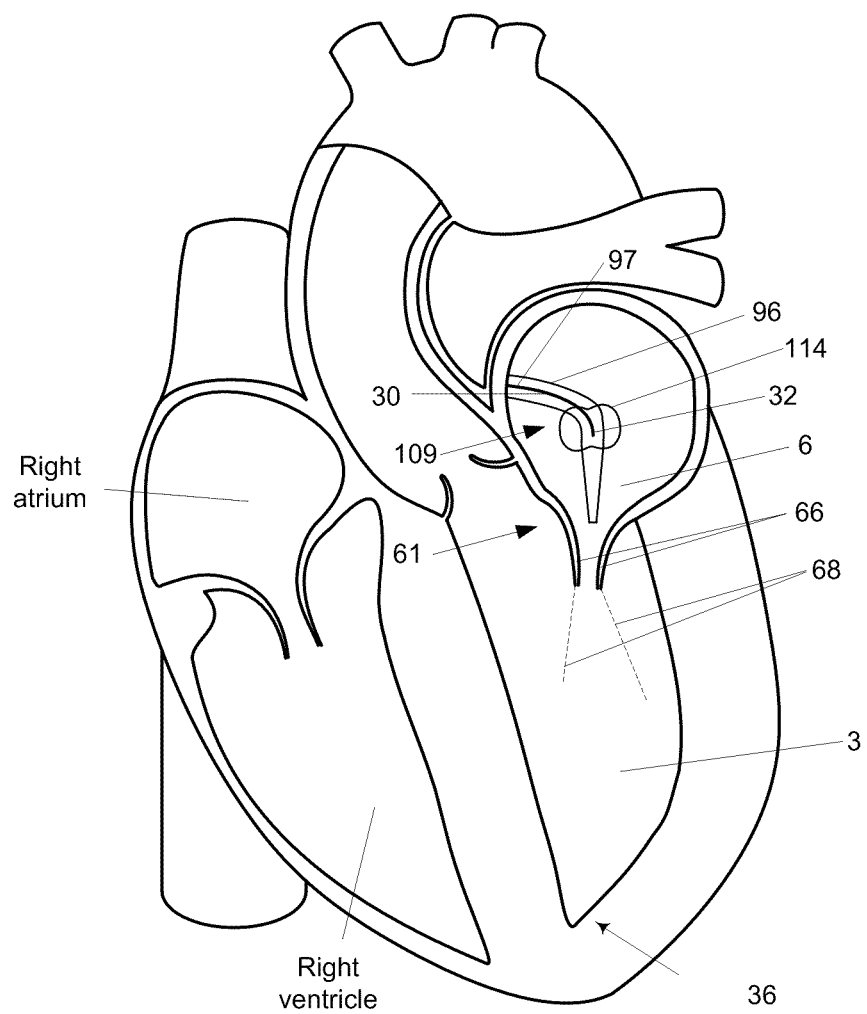
FIG. 16 illustrates a perspective view of a dilator in the inflated or expanded position located in the left atrium prior to passing through the mitral valve consistent with the present disclosure.

Turning now to FIG. 15, the dilator 34 may be advanced over the delivery guide wire 30 proximate to the tip 32 of the delivery guide wire 30. The tip 32 may still extend beyond the tip 98 of the dilator 34 to protect the atrial wall from perforation. According to one embodiment, the expanding portion 114 may be expanded as generally illustrated. The dilator 34 may aimed generally towards the mitral valve 61 as generally illustrated in FIG. 16. For example, the tip 98 may be bent or curved by actuating one or more knobs or the like (not shown) to move one or more deflecting wires as discussed herein. The tip 32 of the delivery guide wire 30 may optionally be retracted into the lumen 97 of the dilator 34 to increase the flexibility of the distal tip region 109. The curvature of the dilator 34 may be confirmed using fluoroscopic and/or echo guidance techniques or the like. For example, the contrast media and/or the radiopaque markers may be used.

Figure 17:
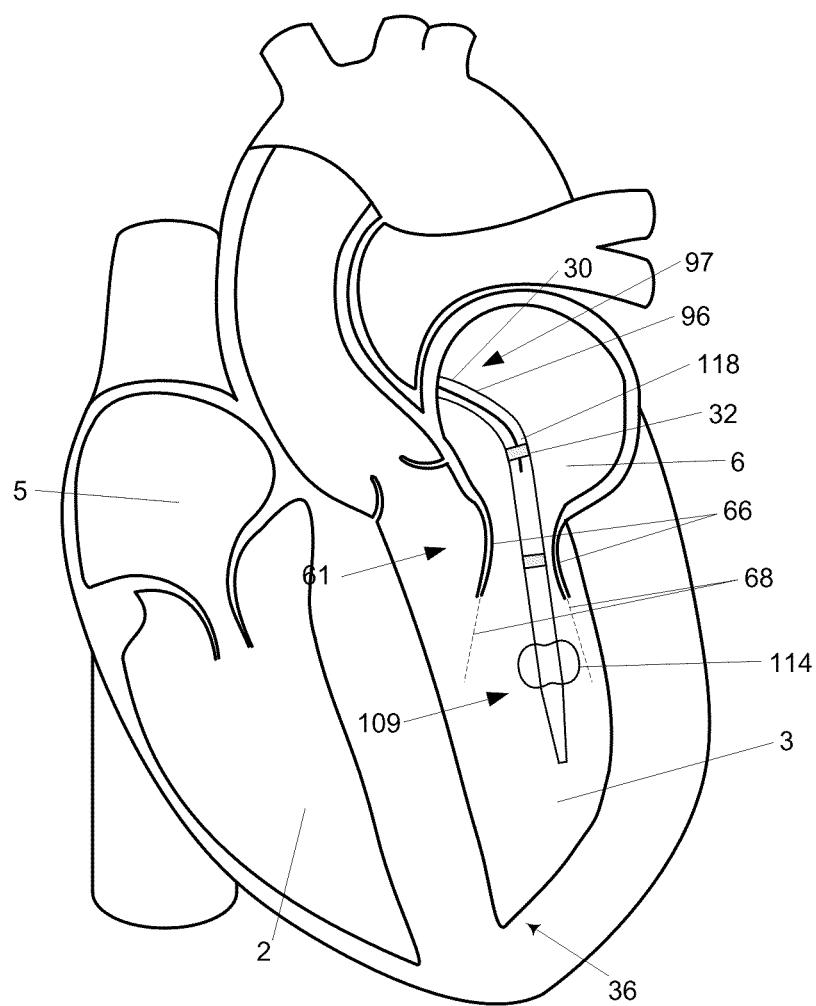
FIG. 17 illustrates a perspective view of a dilator located in the left ventricle consistent with the present disclosure.

Turning now to FIG. 17, with the dilator 34 aimed at the mitral valve 61 and the expanding portion 114 inflated, the distal end region 109 of the dilator 34 may be advanced through the mitral valve 61. It should be understood that the dilator 34 may be advanced through the mitral valve without either the deflectable tip 98 and/or the expandable portion 114; however, the use of one or more of the deflectable tip 98 and/or the expandable portion 114 may reduce the potential of damaging the heart 1 and/or getting entangled within the mitral valve 61. The second segment 97b of the shaft 96 may generally correspond to the location of the bend or curve of the dilator 34 proximate the transseptal puncture site 13. As may be appreciated, the necessary curvature of the dilator 34 between the transseptal puncture site 13 and the left ventricle 3 is relatively sharp.

The tip 32 of the delivery guide wire 30 may be still located inside the lumen 97 of the dilator 34 back in the left atrium 6 generally where it was located in FIG. 16. The dilator 34 may not yet be aimed or directed at the intended implantation site at this point. Instead, it is only important that the distal end region 109 of the dilator 34 is through the mitral valve 61 without damaging and/or entangling the cusps 66 and the chordae/papillary muscles 68.

Figure 18:
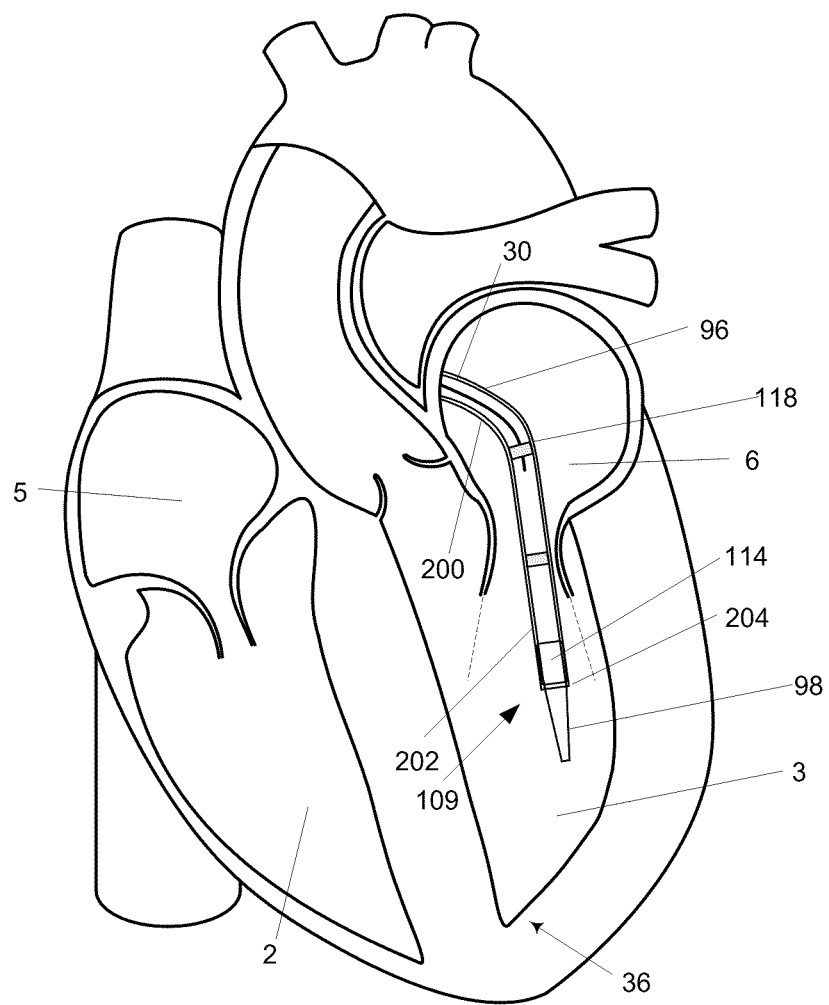
FIG. 18 illustrates a perspective view of an embodiment of a steerable catheter advanced over the dilator in the left ventricle consistent with the present disclosure.

Turning now to FIG. 18, the expandable portion 114 may be retracted/deflated and a steerable catheter 200 may be advanced over the dilator 34 into the left ventricle 3 proximate to the distal end region 109 of the dilator 34. The steerable catheter 200 may define at least one lumen 202 configured receive the dilator 34 as generally illustrated. The lumen 202 may also be configured to receive an implant (not shown) such as, but not limited to, a mitral valve implant as generally disclosed in U.S. patent Ser. No. 11/940,724 filed Nov. 15, 2007 and U.S. patent application Ser. No. 12/209,686 filed Sep. 12, 2008, both of which are fully incorporated herein by reference. The steerable catheter 200 may also be configured to be selectively curved or bent to facilitate aiming of the distal tip 204 for securing the implant and/or facilitate removal of the steerable catheter 200.

Figure 19:
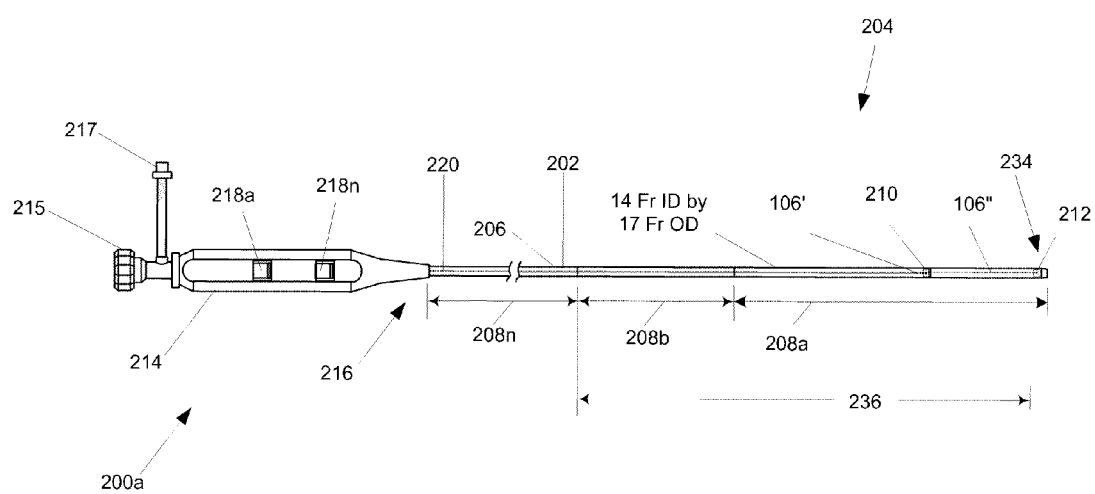
FIG. 19 illustrates a perspective view of one embodiment of a steerable catheter consistent with the present disclosure.

One embodiment of a steerable catheter 200a is generally illustrated in FIG. 19. The steerable catheter 200a may include shaft 206 defining at least one lumen 202. The lumen 202 may be configured to receive the dilator 34 and/or an implant (not shown). The shaft 206 may also include a plurality of segments or portions 208a-208n having different hardness or stiffness to produce the desired overall curvature. The shaft 206 may be formed from one or more suitable polymers such as, but not limited to, a polyether block amide. The shaft 206 may have a constant inner and/or outer diameter and may be made from different materials to provide the various stiffness or hardness. Alternatively, or in addition, the shaft 206 may have different inner and/or outer diameters and may be made from one or more materials. For example, the various stiffness or hardness of the shaft 206 may be provided by varying the thickness of the shaft 206 at the different segments or portions. The different hardness of the segments may provide differing degrees of bending stiffness to the steerable catheter 200a which may facilitate advancing the steerable catheter 200a into and/or out of the left ventricle 3 as well as aiming or alignment of the steerable catheter 200a.

As shown, the steerable catheter 200a may comprise three different segments 208a, 208b and 208n. The first segment 208a may be disposed proximate the distal tip 204. The first segment 208a may optionally include the tapered tip 209 and may have a length of approximately 8 inches. The tapered tip 209 may be provided to facilitate advancing the steerable catheter 200a into the percutaneous puncture site in the groin and over the dilator 34.

According to at least one embodiment, the first segment 208a may be formed of PEBAX™ 2533 having a durometer of 25 D and may have a length of approximately 4 to 6 inches. The second segment 208b may be adjacent to the first segment 208a and may have a length of approximately 2.5 inches. According to at least one embodiment, the second segment 208b may be formed of PEBAX™ 4033 having a durometer of 40 D. The third segment 208n may be adjacent to the second segment 208b and may have a length sufficiently long to extend beyond the access incision. According to at least one embodiment, the third segment 208n may be formed of PEBAX™ 7233 having a durometer of 72 D.

It should be understood that the various lengths and hardness described above for the segments 208a-208n may be adjusted or changed depending upon the circumstances of its intended use. For example, patients with larger and/or smaller hearts may require one or more of the segments to be longer or short. An important aspect of the segments 208a-208n is that the softest segment is the first segment 208a. Also, the second segment 208b is disposed approximately 4 to 6 inches from the distal tip 209. As will be explained herein, the length of the first segment 208a may generally correspond to the length between the transseptal puncture site 13 and the implantation site (e.g., the apex) in the left ventricle 3 where the curvature of the steerable catheter 200a may be greatest.

The steerable catheter 200a may also include a first steering device 210. The first steering device 210 may include a pull ring or the like which may be disposed about 1.5-4 inches from the distal end of the tip 209. The exact length of the first steering device 210 from the tip 209 may depend on the size of the patient's heart which may vary quite a bit depending on, among other things, the degree of regurgitation. For example, patients with functional mitral regurgitation often have dilated cardiomyopathy (enlarged left ventricle). According to at least one embodiment, the first steering device 210 may be located 2 inches from the tip 209.

The steerable catheter 200a may optionally include at least a second steering device 212. The second steering device 212 may include a pull ring or the like which may be disposed proximate to the distal end of the tip 209. The second or more steering devices 212 may be provided to facilitate curving or bending of the steerable catheter 200a. The first and second steerable devices 210, 212 may be configured to reduce drag during withdrawal and may also facilitate alignment or aiming of the tip 209 within the left ventricle 3. The first and second steerable devices 210, 212 may also facilitate advancement of the steerable catheter 200a over the dilator 34, through the transseptal puncture site 13, and through the left atrium 6 and down into the left ventricle 3.

The first and/or second steerable devices 210, 212 may be coupled to a handle assembly 214 which may be disposed about a proximal end 216 of the shaft 206. The handle assembly 214 may include one or more fittings and/or valves. For example, the handle assembly 214 may include a valve 215 (for example, but not limited to, a hemostasis valve or the like) and/or a fitting 217 (for example, but not limited to, a luer lock fitting or the like). The handle assembly 214 may also include one or more actuation devices 218a-218n (such as, but not limited to, knobs, sliders, or the like) coupled to the first and second steerable devices 210, 212. The actuation devices 218a-n may be configured to place the first and second steerable devices 210, 212 under tension, therefore causing the shaft 206 to deflect (e.g., curve or bend). For example, the steerable catheter 200b may include actuation devices 218a-n coupled to the first and/or second steerable devices 210, 212 by way of one or more wires or the like 220 disposed along at least a portion of the shaft 206 as generally illustrated in FIGS. 20A-20D.

By way of example, the actuation devices 218a-n may be slide distally and/or proximally within the handle assembly 214 to increase or decrease the tension placed on the wires 220. The tension in the wires 220 may asymmetrically urge/pull the first and/or second steerable devices 210, 212 (e.g., the first and/or second pull rings) to one side causing the shaft 206 to defect or curve where the wires 220 are coupled to the first and/or second steerable devices 210, 212.

Turning now specifically to FIGS. 20C-20D, the shaft 206 may optionally include an inner layer 230 configured to provide a substantially seamless inner surface of the lumen 202. The inner layer 230 may also be configured to reduce and/or minimize surface friction. According to at least one embodiment, the inner layer 230 may include PTFE or the like. The shaft 206 may also include another layer 232 configured to provide the desired stiffness. For example, the layer 232 may include Pebax™ or the like.

Optionally, the shaft 206 may include three or more sections configured to provide kink resistance, pushability, and/or flexibility. For example, the shaft 206 may include a reinforced section 234 disposed between the first steering device 210 and the second steering device 212. The reinforced section 234 may be configured to provide increased flexibility, which may facilitate navigating the shaft 206 to the left ventricle 3 and configured to provide increased kink resistance. According to at least one embodiment, the reinforced section 234 may be spiral reinforced and may have a length of 1-3 inches.

The shaft 206 may also optionally include spiral reinforced section 236 (as generally illustrated in FIGS. 19 and 20C). The spiral reinforced section 236 may extend from the first steering device 210 towards the handle assembly 214 for about 7.5 inches. The spiral reinforced section 236 may be configured to provide kink resistance when deflecting the shaft 206 using the first and/or second steerable devices 210, 212. As may be appreciated, a kink in the shaft 206 may reduce the ability of the user to locate the distal tip 209 within the left ventricle 3 and may also increase the force needed to push the implant through the lumen 202 during deployment.

The shaft 206 may also optionally include a braided reinforced section 238. The braided reinforced section 238 may extend from the proximal end of the spiral reinforced section 236 to the handle assembly 214. The braided reinforced section 238 may be configured to increase the pushability and torsional strength of the shaft 206 while reducing and/or minimizing kinking. Increasing the pushability and torsional strength and preventing kinking may be important since the length of the shaft 206 from the groin (where the steerable catheter 204 may be introduced) to the left ventricle 3 may be fairly long and involve tortuous anatomy.

Turning now to FIGS. 21-24, the effects of actuating the first and/or second steerable devices 210, 212 on the shaft 206 are generally illustrated. For example, FIG. 21 generally illustrates one embodiment of a steerable catheter 202a in which the shaft 206 is unbiased. FIG. 22 generally illustrates deflection of the distal region 240. For example, a user may actuate the second actuation device 218n (for example, but not limited to, by sliding the second actuation device 218n generally in the direction of arrow A) causing the second steerable device 212 to deflect the shaft 206 in a region 240 proximate the second steerable device 212. As may be seen, the second steerable device 212 may cause the shaft 206 to deflect and/or bend in a region 240 between the second steerable device 212 and the handle assembly 214. According to at least one embodiment, the second steerable device 212 may generally cause the shaft 206 to deflect and/or bend in a region 240 between the second steerable device 212 and the first steerable device 210. The second steerable device 212 may generally cause the shaft 206 to deflect and/or bend up to approximately 180 degrees, though angles of curvature greater than 180 degrees are also possible depending on flexibility of the shaft 206 as well as the effects of the shaft 206 needing to bend passively to accommodate the patient's anatomy. The radius of the curvature may be 1.0 inches to 2.0 inches, for example, 1.25 inches to 1.75 inches.

FIG. 23 generally illustrates deflection of the proximal region 242. For example, a user may actuate the first actuation device 218a (for example, but not limited to, by sliding the first actuation device 218a generally in the direction of arrow B) causing the first steerable device 210 to deflect the shaft 206 in a region 242 proximate the first steerable device 210. As may be seen, the first steerable device 210 may cause the shaft 206 to deflect and/or bend in a region 242 between the first steerable device 210 and the handle assembly 214. According to at least one embodiment, the first steerable device 210 may generally cause the shaft 206 to deflect and/or bend up to approximately 180 degrees, though angles of curvature greater than 180 degrees are also possible depending on flexibility of the shaft 206 as well as the effects of the shaft 206 needing to bend passively to accommodate the patient's anatomy. The radius of the curvature may be 1.0 inches to 2.0 inches, for example, 1.25 inches to 1.75 inches.

Turning now to FIG. 24, one embodiment generally illustrating the deflecting of both the first and second steering actuators 210, 210 is shown. The first and second steerable devices 210, 212 may generally cause the shaft 206 to deflect and/or bend up to approximately 180 degrees, though angles of curvature greater than 180 degrees are also possible depending on flexibility of the shaft 206 as well as the effects of the shaft 206 needing to bend passively to accommodate the patient's anatomy. The radius of the curvature may be 1.0 inches to 2.0 inches, for example, 1.25 inches to 1.75 inches, however, the exact range of the radius may depend upon the location of the first and second steerable devices 210, 212 as well as the flexibility of the regions 240, 242.

Figure 25:
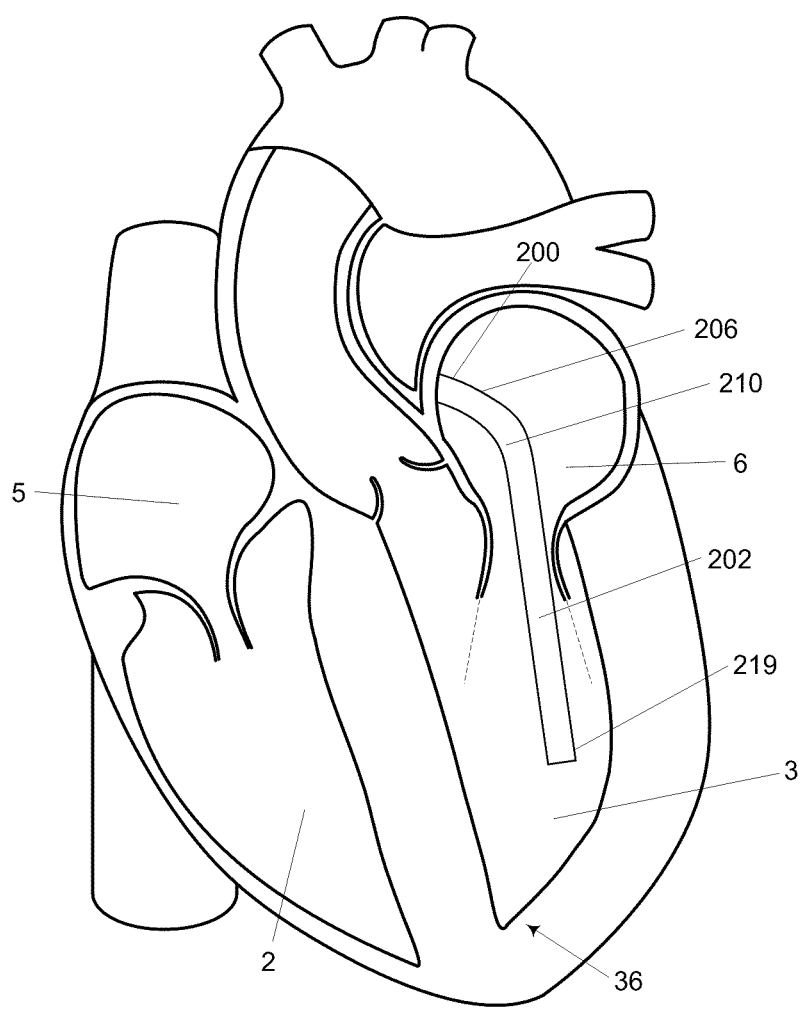
FIG. 25 illustrates a perspective view of an embodiment of a steerable catheter advanced in the left ventricle with an implant loaded consistent with the present disclosure.
Figure 26:
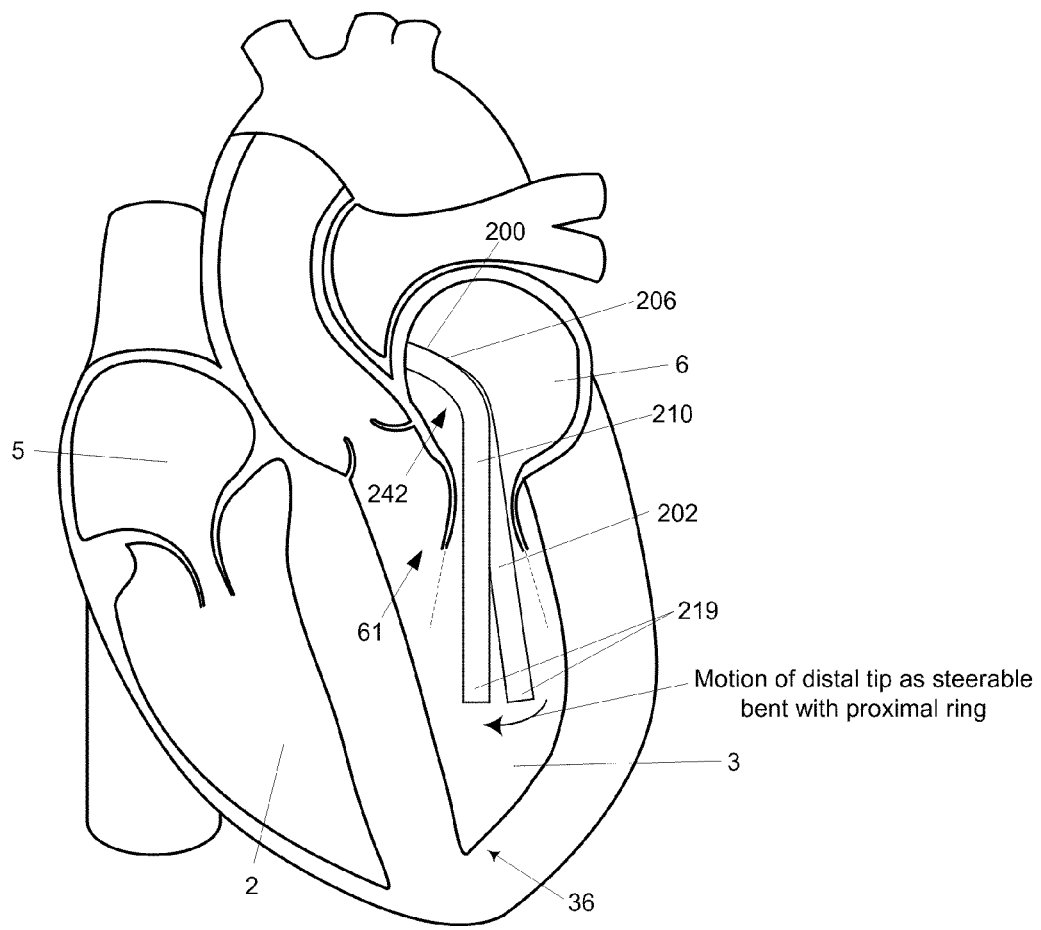
FIG. 26 illustrates a perspective view of an embodiment of a steerable catheter being aimed or aligned with the implant site consistent with the present disclosure.

Turning now to FIG. 25, the dilator 34 has been removed from the steerable catheter 200 and the implant (not shown) may be advanced through the lumen 202 proximate to the distal end 219. By actuating the first steerable actuator 210, the user may aim and/or align the distal end segment and/or distal tip 219 of the steerable catheter 200 to the desired location within the left ventricle 3 where it is desired to anchor or secure the implant by deflecting the shaft 206 in the region 242 as generally illustrated by the arrows in FIG. 26 representing the deflection of the steerable catheter 200. Fluoroscopic and/or echo guidance may be used to facilitate aiming of the steerable catheter 200 within the left ventricle 3.

As may be appreciated, the location of the first steerable actuator 210 and the region 242 along the shaft 206 may generally correspond to the position of the shaft 206 within the left atrium 6 and/or the left ventricle 3 proximate to the mitral valve 61. Ideally, the proximal ring 210 would reside somewhere between the annulus of the valve and the valve leaflets. This would provide for the distal section 234 to be pointed relatively straight at the desired anchor location. The differing lengths of the first section 234 may compensate for the variations in the patients' valve to apex length, although anchoring directly in the apex may not always be the desired location. In FIG. 26 the illustrated bend in the catheter may be closer to the valve.

Figure 27:
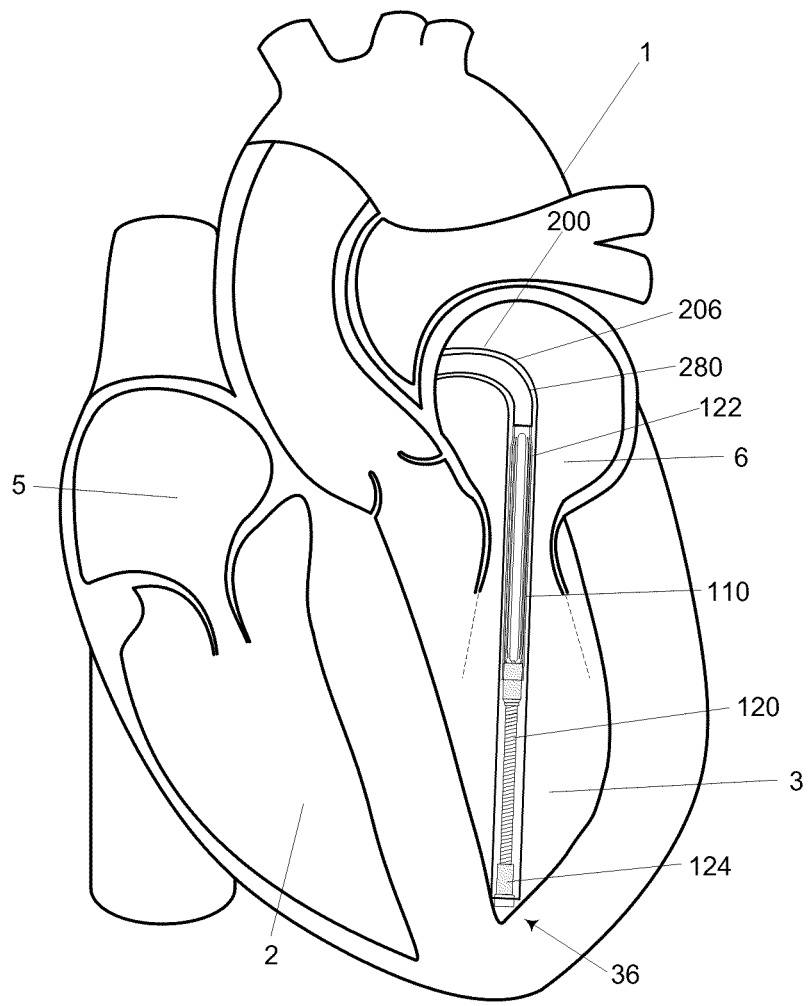
FIG. 27 illustrates a perspective view of an embodiment of a steerable catheter advanced to the implant site consistent with the present disclosure.

Turning now to FIG. 27, once the steerable catheter 200 has been positioned to the desired location within the left ventricle 3 (for example, but not limited to, the apex 36), the implant 110 may be anchored and/or secured to the native tissue. According to one embodiment, the implant 110 may include a shaft 120 coupled to a spacer 122 and an anchoring device 124 as generally illustrated in FIG. 27 and described in U.S. patent Ser. No. 11/940,724 filed Nov. 15, 2007 and U.S. patent application Ser. No. 12/209,686 filed Sep. 12, 2008, both of which are fully incorporated herein by reference. However, the implant 110 may include any other device configured to be received within the lumen 202 of the delivery catheter and/or delivered to the heart 1.

The implant 110 may optionally be advanced through the lumen 202 of steerable catheter 200 using a pusher 280 or the like. Securing the implant 110 to the tissue may depend upon the specifics of the design of the implant 110. For example, the implant 110 may be secured to the tissue using one or more screws (for example, but not limited to, helical screws or the like), tines, and/or sutures (such as, but not limited to, one or more sutures formed, at least in part, of a shape memory alloy).

Once the implant 110 has been secured to the tissue, the steerable catheter 200 may be removed from the left ventricle 3 and ultimately from the heart 1 and the patient's body. According to one embodiment, the steerable catheter 200 may be removed by urging the steerable catheter 200 proximally (i.e., away from the left ventricle 3). The first steering actuator 210 may be used to minimize the force applied against the implant 110 by the steerable catheter 200 as the implant 110 exits the lumen 202 of the steerable catheter 200. If the force applied to the implant 110 by the steerable catheter 200 as the implant 110 exits the lumen 202 of the steerable catheter 200 is too great, damage may occur to the heart 1 proximate to the implant site and/or the implant 110 may be accidentally pulled out and/or disconnected from the tissue.

According to one embodiment, the force applied to the implant 110 by the steerable catheter 200 as the implant 110 exits the lumen 202 of the steerable catheter 200 may be further reduced with the aid of the second or more steerable actuators 212. For example, turning to FIGS. 28-30, one embodiment generally illustrating the deflection withdrawal sequence of a steerable catheter 200 having at least a first and a second steerable actuator 210, 212 is shown. FIG. 28 generally illustrates one embodiment of the steerable catheter 200. The implant 110 (not shown) has been secured to the tissue. The second steerable actuator 212 is illustrated in the "straight" position (i.e., the second steerable actuator 212 is not urging the shaft 206 of the steerable catheter 200). The region 240 between the second steerable actuator 212 and the first steerable actuator 210 (for example, but not limited, the distal most 3 inches of the shaft 206) is over the implant 110 from the apex 36 of the left ventricle 3 up to the mitral valve 61. The first steerable actuator 210 is in the bent or curved position to deflect the shaft 206 in order to accommodate the curve or bend from the mitral valve 60, through the transseptal puncture site 13, and into the right atrium 5.

As the steerable catheter 200 is withdrawn from the left ventricle 3, the region 240 of the steerable catheter 200 may start to encounter the curvature in the left atrium 6 between the mitral valve 61 and the transseptal puncture site 13. In order to accommodate this curvature, the second actuation device 212 may be actuated to deflect the region 240 of the shaft 206 of the steerable catheter 200 as generally illustrated in FIG. 29. Deflecting the region 240 of the shaft 206 may reduce drag of the steerable catheter 200 on the implant 110 and may also reduce the likelihood of dislodging the implant 110 from the tissue. While deflecting the region 240, the user may also un-bend the region 242 of the shaft 206 as the region 242 is moving through the transseptal puncture site 13 and into a region of reduced curvature. As the steerable catheter 200 is further removed, the second actuation device 212 may be un-bent to un-bend the region 240 of the shaft 206 as it moves through the transseptal puncture site 13 as generally illustrated in FIG. 30. At this point, both regions 240, 242 of the shaft 206 may be somewhat curved passively by the anatomy alone.

Accordingly, the present disclosure may include a steerable catheter including a first steerable actuator disposed 1.5-4 inches from the distal tip of the shaft. The first steerable actuator may include, but is not limited to, a pull ring or the like. The steerable catheter having a first steerable actuator may facilitate aiming or positioning the tip of the steerable catheter to the desired location within the left ventricle. The first steerable actuator may also reduce the force exerted on the implant by the shaft when removing steerable catheter from the left ventricle and may also reduce damage to the heart by allowing the shaft to better conform to the geometries of the pathway.

The steerable catheter may optionally include at least a second steerable actuator in addition to the first steerable actuator. The second steerable actuator may include, but is not limited to, a pull ring or the like which may be positioned proximate to the distal tip of the shaft. The second steerable actuator may further reduce the force exerted on the implant by the shaft when removing steerable catheter from the left ventricle and may also reduce damage to the heart by allowing the shaft to better conform to the geometries of the pathway. The first and/or second steerable actuators may also facilitate advancing the steerable catheter over a dilator through the tortuous pathway of the transseptal route to the left ventricle.

The present disclosure may also include a dilator having a plurality of segments having different hardness or stiffness. The different segments may improve the ability of the steerable catheter to be inserted over the dilator through the tortuous pathway of the transseptal route to the left ventricle. According to at least one embodiment, the dilator may include four segments wherein the softest segment is located approximately 6 inches from the distal tip.

The dilator may optionally include an expandable device (such as, but not limited to, a balloon or the like) disposed proximate the distal tip. The expandable device may facilitate advancing the dilator through the mitral valve without damaging the mitral valve (for example, damaging and/or becoming entangled in the cusps and/or papillary muscles). The dilator may also optionally include a deflectable tip. The deflectable tip may improve the general control of the dilator as it is advanced over a guide wire the transseptal route to the left atrium. The deflectable tip may also allow the expandable device to be aimed towards the mitral valve, further facilitating the advancement to the dilator through the mitral valve.

An implant consistent with the present disclosure may also comprise other embodiments, for example, but not limited to, one or more of the implants as described in U.S. patent application Ser. Nos. 11/258,828 filed Oct. 26, 2005 and entitled HEART VALVE IMPLANT; 11/940,724 filed on Nov. 15, 2007 and entitled HEART REGURGITATION METHOD AND APPARATUS; 11/748,121 filed on May 14, 2007 and entitled BALLOON MITRAL SPACER; 11/748,138 filed on May 14, 2007 and entitled SOLID CONSTRUCT MITRAL SPACER; 11/940,674 filed on Nov. 15, 2007 and entitled MITRAL SPACER; 11/748,147 filed on May 14, 2007 and entitled SAFETY FOR MITRAL VALVE PLUG; and 11/940,694 filed on Nov. 15, 2007 and entitled IMPLANT DELIVERY SYSTEM AND METHOD, all of which are fully incorporated herein by reference.

The steerable catheter and/or dilator disclosed herein may be used to deliver an implant. As described above, a heart valve implant consistent with the present disclosure may be used in the treatment mitral valve regurgitation. However, the heart valve implant as well as its associated methods may also suitably be employed in other applications, e.g., as an implant associated with one of the other valves of the heart, etc. The present disclosure should not, therefore, be construed as being limited to use for reducing and/or preventing regurgitation of the mitral valve.

As mentioned above, the present disclosure is not intended to be limited to an apparatus, system or method which must satisfy one or more of any stated or implied object or feature of the present disclosure and should not be limited to the preferred, exemplary, or primary embodiment(s) described herein. The foregoing description of the present disclosure has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure when interpreted in accordance with breadth to which it is fairly, legally and equitably entitled.

What is claimed is:

1. A catheter, comprising:
    a handle;
    a shaft comprising a proximal end and a distal end, said proximal end coupled to said handle; and
    first and second steerable actuators coupled to said shaft so as to define a first region between said first steerable actuator and said proximal end, a second region between said first and second steerable actuators, and a third region between said distal end and said second steerable actuator;
  wherein:
    said handle comprises first and second actuators coupled to said first and second steerable actuators, respectively, said first actuator configured to apply a force to said first actuator and deflect said shaft in said second region, said second actuator configured to apply a force to said second actuator and deflect said shaft in said third region;
    said first region comprises a spiral reinforced section extending from said first steerable actuator towards said handle;
    said first region further comprises a braided reinforced section extending from a proximal end of said spiral reinforced section towards said handle; and
    said first region remains substantially straight during the deflection of one or both of said second and third regions.

2. The catheter of claim 1, wherein:
    said shaft further comprises a lumen; and
    said catheter further comprises a dilator configured to be received within said lumen.

3. The catheter of claim 1, wherein:
    said shaft further comprises a lumen; and
    said catheter further comprises an implant configured to be received within said lumen.

4. The catheter of claim 1, wherein said first steerable actuator is configured to deflect said second region of said shaft to form a first curve up to 180 degrees, and said second steerable actuator is configured to deflect said third region of said shaft to form a second curve of up to 180 degrees.

5. The catheter of claim 1, wherein said second actuator comprises a second pull ring coupled to said shaft.

6. The catheter of claim 5, wherein said second actuator is coupled to said second pull ring with at least a second wire.

7. The catheter of claim 1, wherein said first steerable actuator is configured to deflect said second region of said shaft to form a first curve up to 180 degrees.

8. The catheter of claim 7, wherein said first curve comprises a radius of between 1.0 inches and 2.0 inches.

9. The catheter of claim 8, wherein said first curve comprises a radius of between 1.25 inches and 1.75 inches.

10. The catheter of claim 1, wherein said second steerable actuator is configured to deflect said third region of said shaft to form a second curve of up to 180 degrees.

11. The catheter of claim 10, wherein said second curve comprises a radius of between 1.0 inches and 2.0 inches.

12. The catheter of claim 11, wherein said second curve comprises a radius of between 1.25 inches and 1.75 inches.

13. The catheter of claim 1, wherein:
said catheter is configured to extend through a transseptal puncture site, a left atrium, a mitral valve, and into a left ventricle:
said shaft comprises at least one lumen configured to receive at least one of an implant and a dilator; and
said first steerable actuator is coupled to said shaft at a position on said shaft substantially corresponding to said transseptal puncture site when said shaft is disposed through said transseptal puncture site, through said left atrium, and through said mitral valve, such that the distal end of said shaft is disposed within said left ventricle.

14. The catheter of claim 13, wherein said position corresponds to 1.5 to 4 inches from said distal end.

15. The catheter of claim 14, wherein said position corresponds to 3 inches from said distal end.

16. The catheter of claim 1, wherein said first steerable actuator comprises a first pull ring coupled to said shaft.

17. The catheter of claim 16, wherein said first actuator is coupled to said first pull ring with at least a first wire.

18. The catheter of claim 17, wherein said shaft comprises a first lumen configured to receive at least one of an implant and a dilator and a second lumen, wherein the first wire is disposed within the second lumen.

19. The catheter of claim 1, wherein:
said first region is adjacent said second region;
said second region is adjacent said first and third regions;
said third region is adjacent said second region;
the first, second and third regions have first, second, and third stiffnesses, respectively; and
the first stiffness differs from the second stiffness, the second stiffness differs from the first stiffness and third stiffness, and the third stiffness differs from the second stiffness.

20. The catheter of claim 19, wherein the third stiffness is lower than the first stiffness and second stiffness, and the third stiffness is higher than the first stiffness and second stiffness.

21. The catheter of claim 20, wherein said third section is 8 inches long and the second section is 2.5 inches long.

22. The catheter of claim 20, wherein said third section has a durometer of 25 D, said second section has a durometer of 40 D, and said first section has a durometer of 72 D.

* * * * *